(12) United States Patent
Devengenzo et al.

(10) Patent No.: US 11,767,902 B2
(45) Date of Patent: Sep. 26, 2023

(54) BELT TERMINATION AND TENSIONING IN A PULLEY ARRANGEMENT FOR A ROBOTIC ARM

(71) Applicant: Verb Surgical Inc., Santa Clara, CA (US)

(72) Inventors: Roman Devengenzo, San Jose, CA (US); Matthew Reagan Williams, Walnut Creek, CA (US); Stephen John Morfey, Santa Clara, CA (US); Ricardo Alfonso León, San Jose, CA (US); Andrew Metzger, Oakland, CA (US); Karen Shakespear Koenig, San Jose, CA (US); Vijay Soundararajan, Santa Clara, CA (US)

(73) Assignee: Verb Surgical Inc., Santa Clara, CA (US)

( * ) Notice: Subject to any disclaimer, the term of this patent is extended or adjusted under 35 U.S.C. 154(b) by 0 days.

(21) Appl. No.: 17/732,842

(22) Filed: Apr. 29, 2022

(65) Prior Publication Data
US 2022/0250259 A1  Aug. 11, 2022

Related U.S. Application Data

(62) Division of application No. 15/706,582, filed on Sep. 15, 2017, now Pat. No. 11,345,053.

(Continued)

(51) Int. Cl.
*F16H 19/06* (2006.01)
*B25J 9/10* (2006.01)
(Continued)

(52) U.S. Cl.
CPC ........ *F16H 19/0672* (2013.01); *B25J 9/1045* (2013.01); *F16H 55/52* (2013.01);
(Continued)

(58) Field of Classification Search
CPC .... B25J 9/1045; F16H 19/0672; F16H 55/52; F16H 2019/0668; F16H 2019/0677; F16H 7/08; F16H 9/14
See application file for complete search history.

(56) References Cited

U.S. PATENT DOCUMENTS 2,212,823 A   8/1940  Bulk
4,478,594 A * 10/1984 Gayer .................... F16H 55/54
                                                           474/54

(Continued)

FOREIGN PATENT DOCUMENTS

CN     102764159 A    11/2012
CN     104717935 A    6/2015
(Continued)

OTHER PUBLICATIONS

Office Action for Brazilian Application No. BR112019004223-7 dated Feb. 22, 2022, 5 pages.
(Continued)

*Primary Examiner* — Bobby Rushing, Jr.
(74) *Attorney, Agent, or Firm* — Aikin & Gallant, LLP

(57) ABSTRACT

In one variation, a pulley arrangement includes a base pulley portion rotatable within a driving plane, an adjustable pulley portion coupled to the base pulley portion wherein the adjustable pulley portion is rotatable relative to the base pulley portion within the driving plane, and a driving member including an end coupled to the adjustable pulley portion wherein at least a portion of the driving member is wrapped at least partially around the adjustable pulley portion. In another variation, a pulley arrangement includes a base pulley portion rotatable around an axis, an adjustable pulley portion coupled to the base pulley portion and movable in a first direction parallel to the axis, and a sliding block engaged with the adjustable pulley portion, wherein the sliding block moves in a second direction different from (Continued)

the first direction, in response to compression of the adjustable pulley portion against the base pulley portion.

20 Claims, 20 Drawing Sheets

Related U.S. Application Data

(60) Provisional application No. 62/395,704, filed on Sep. 16, 2016.

(51) Int. Cl.
   *F16H 55/52* (2006.01)
   *F16H 19/00* (2006.01)

(52) U.S. Cl.
   CPC .... *F16H 19/005* (2013.01); *F16H 2019/0668* (2013.01); *F16H 2019/0677* (2013.01)

(56) References Cited

U.S. PATENT DOCUMENTS

| | | | |
|---|---|---|---|
| 4,539,000 A * | 9/1985 | Gayer | F16H 55/563 474/11 |
| 4,552,028 A | 11/1985 | Burckhardt et al. | |
| 4,568,371 A | 2/1986 | Nebelung et al. | |
| 5,150,759 A | 9/1992 | Borchard | |
| 5,447,076 A | 9/1995 | Ziegler | |
| 5,797,900 A | 8/1998 | Madhani et al. | |
| 6,360,612 B1 | 3/2002 | Trantzas et al. | |
| 6,966,428 B1 | 11/2005 | Flynn | |
| 10,647,007 B2 | 5/2020 | Cordoba et al. | |
| 10,661,453 B2 | 5/2020 | Koenig et al. | |
| 2003/0083648 A1 | 5/2003 | Wang et al. | |
| 2003/0195664 A1 | 10/2003 | Nowlin et al. | |
| 2004/0266574 A1 | 12/2004 | Makoto et al. | |
| 2006/0167440 A1 | 7/2006 | Cooper et al. | |
| 2007/0089557 A1 | 4/2007 | Solomon et al. | |
| 2007/0261894 A1 | 11/2007 | Harish | |
| 2007/0299427 A1 | 12/2007 | Yeung et al. | |
| 2008/0087871 A1 | 4/2008 | Schena | |
| 2008/0190210 A1 | 8/2008 | Harish et al. | |
| 2009/0114041 A1 | 5/2009 | Harish et al. | |
| 2011/0023651 A1 | 2/2011 | Cooper | |
| 2013/0023794 A1 | 1/2013 | Stein et al. | |
| 2013/0325033 A1 | 12/2013 | Schena et al. | |
| 2013/0331644 A1 | 12/2013 | Pandya et al. | |
| 2014/0358162 A1 | 12/2014 | Valdastri et al. | |
| 2015/0038982 A1 | 2/2015 | Kilroy et al. | |
| 2015/0081098 A1 | 3/2015 | Kogan | |
| 2015/0237308 A1 | 8/2015 | Tanaka et al. | |
| 2015/0292969 A1 | 10/2015 | Choi et al. | |
| 2015/0323398 A1 | 11/2015 | Lauzier et al. | |
| 2016/0077638 A1 | 3/2016 | Bulea et al. | |
| 2017/0020615 A1 | 1/2017 | Koenig et al. | |
| 2018/0079090 A1 | 3/2018 | Koenig et al. | |
| 2018/0080841 A1 | 3/2018 | Cordoba et al. | |

FOREIGN PATENT DOCUMENTS

| | | |
|---|---|---|
| WO | 2015/1325149 A1 | 9/2015 |
| WO | 2018/053349 A1 | 3/2018 |
| WO | 2018/053360 A1 | 3/2018 |
| WO | 2018/053361 A1 | 3/2018 |

OTHER PUBLICATIONS

Written Opinion of the International Search Authority dated Jan. 23, 2018 for WO Application No. PCT/US17/051921.
Written Opinion of the International Search Authority dated Dec. 1, 2017 for WO Application No. PCT/US17/051922.
Written Opinion of the International Search Authority dated Dec. 1, 2017 for WO Application No. PCT/US17/051908.
Outgoing—ISA/210—International Search Report dated Jan. 23, 2018 for WO Application No. PCT/US17/051921.
Outgoing—ISA/210—International Search Report dated Dec. 1, 2017 for WO Application No. PCT/US17/051922.
Outgoing—ISA/210—International Search Report dated Dec. 1, 2017 for WO Application No. PCT/US17/051908.
Examiner's Report of the Canadian Patent Office dated Jan. 31, 2020, for Canadian application No. 3,034,639.
Extended European search report of the European Patent Office dated Mar. 26, 2020, for European application No. EP17851669.6.
Australian Examination Report of the Australian Patent Office dated Apr. 23, 2019 for related Australian Patent Application No. 2017326462.
Extended European Search Report of the European Patent Office dated Apr. 2, 2020 for related European Patent Application No. 17851661.3.
Extended European Search Report of the European Patent Office dated May 8, 2020 for related European Patent Application No. 17851670.4.
First Office Action of the Chinese Patent Office dated Jun. 29, 2020 for related Chinese Patent Application No. 201780004133.8.
Notice of Reasons for Refusal of the Japanese Patent Office dated Apr. 24, 2020 for related Japanese Patent Application No. 2019-511440.
Decision to Grant a Patent of the Japanese Patent Office dated Oct. 1, 2020 for related Japanese Patent Application No. 2019-511440.
Notification of Reason for Refusal of the Korean Patent Office dated Sep. 29, 2020 for related Korean Patent Application No. 10-2019-7007189.
Examination Report for Australian Application No. 2020203372 dated May 12, 2021, 4 pages.
Non-Final Office Action for U.S. Appl. No. 17/394,016 dated Oct. 27, 2022, 9 pages.
Non-Final Office Action for U.S. Appl. No. 16/852,213 dated Dec. 21, 2022, 9 pages.
Communication Pursuant to Article 94(3) EPC for European Application No. 17851670.4 dated Nov. 28, 2022, 4 pages.

* cited by examiner

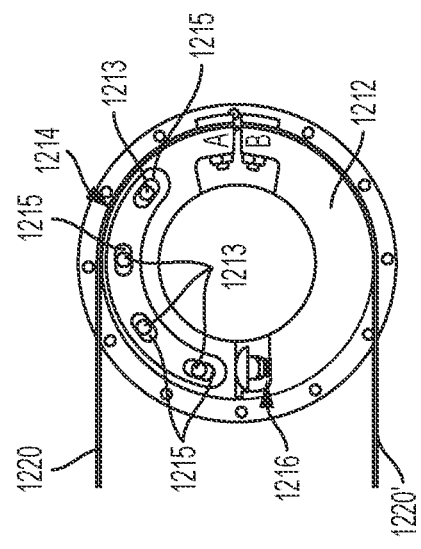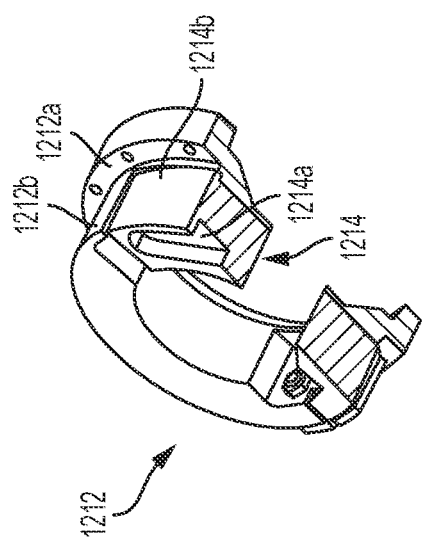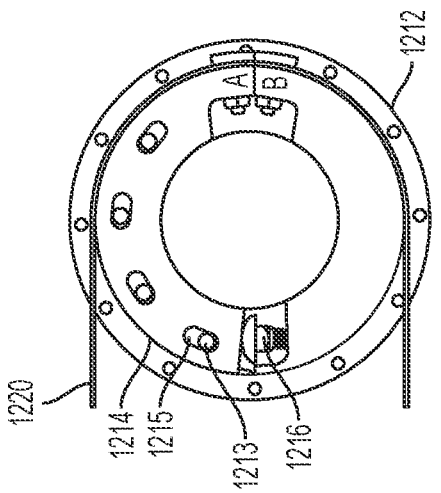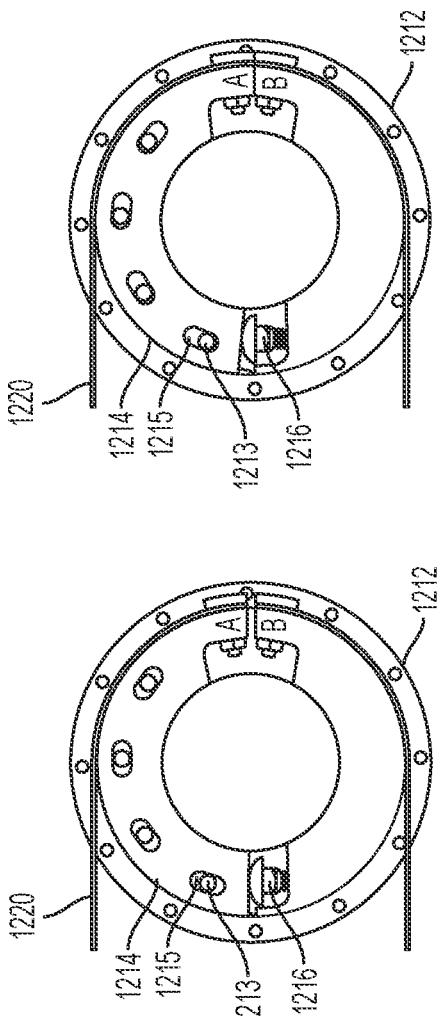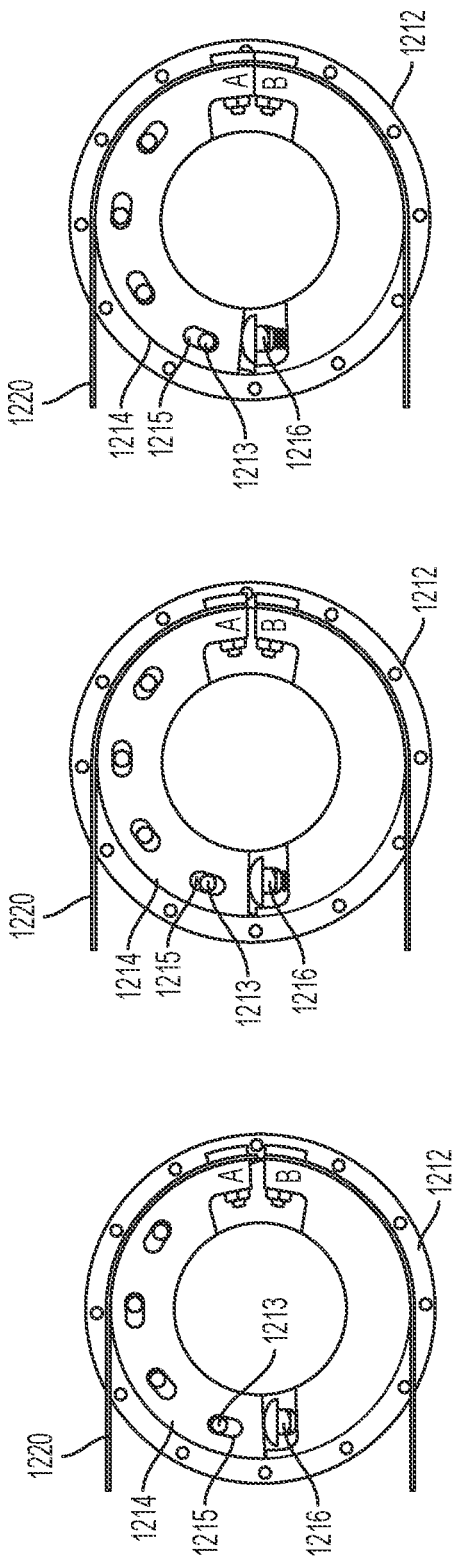
FIG. 12B
FIG. 12C
FIG. 13A
FIG. 13B
FIG. 13C

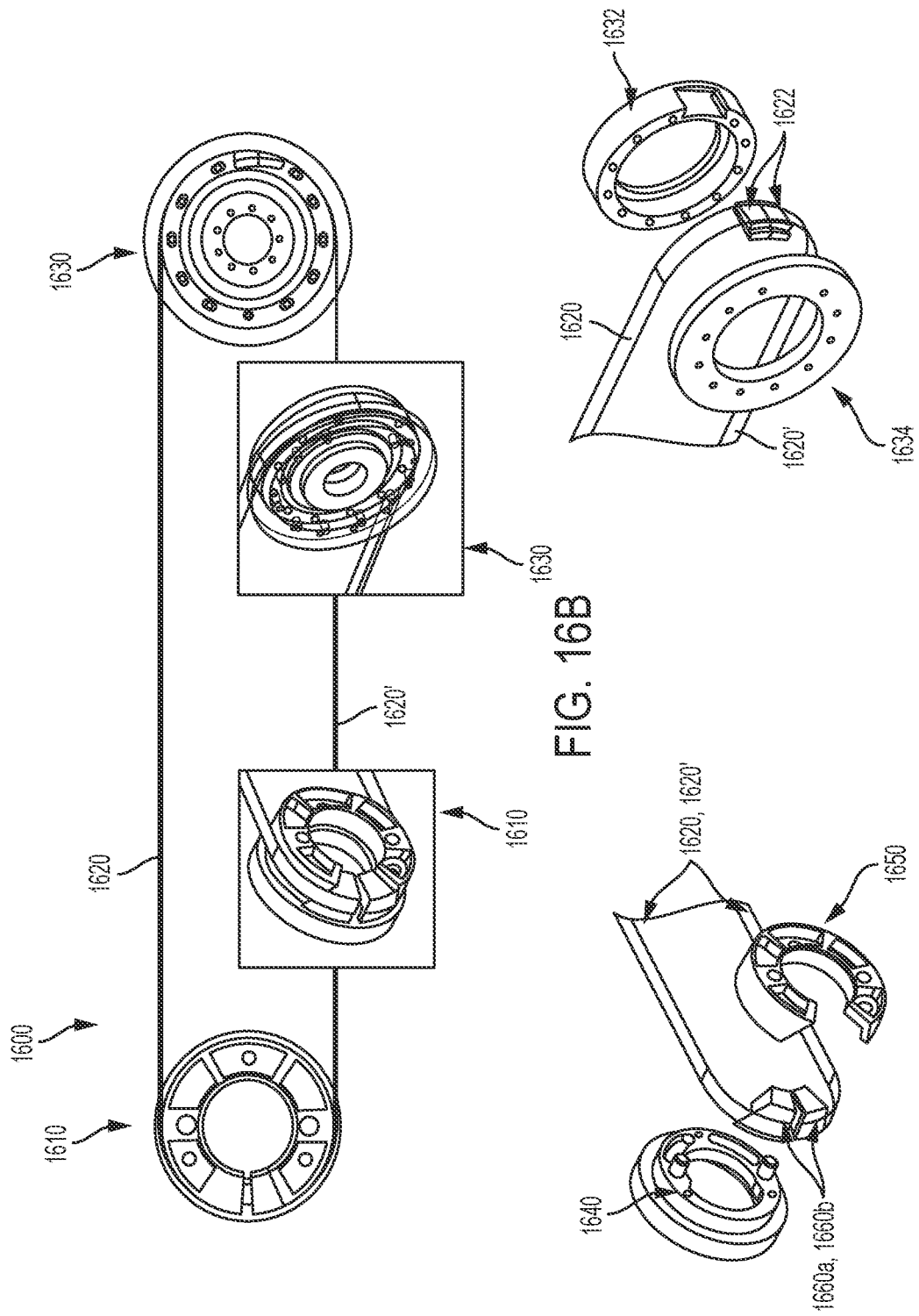

BELT TERMINATION AND TENSIONING IN A PULLEY ARRANGEMENT FOR A ROBOTIC ARM

CROSS-REFERENCE TO RELATED APPLICATIONS

This application is a divisional application of U.S. patent application Ser. No. 15/706,582, filed on Sep. 15, 2017, which claims priority to U.S. Patent Application Ser. No. 62/395,704, filed on Sep. 16, 2016, which is hereby incorporated by this reference in its entirety.

TECHNICAL FIELD

This invention relates generally to the field of robotic arms, and more specifically to pulley arrangements for a robotic arm.

BACKGROUND

Robotic arms are used in a variety of applications, such as in manufacturing and surgical procedures. For example, robotic-assisted minimally-invasive surgery (MIS) involves techniques intended to reduce tissue damage during a surgical procedure. Robotic-assisted laparoscopic procedures, for example, typically involve creating a number of small incisions in the patient (e.g., in the abdomen), and introducing one or more instruments (e.g., one or more tools, at least one camera, etc.) through the incisions into the patient. The surgical procedures are then performed by using the introduced tools controlled by one or more robotic arm assemblies commanded by an operator, with the visualization aid provided by the camera. Generally, MIS provides multiple benefits, such as reduced patient scarring, less patient pain, shorter patient recovery periods, and lower medical treatment costs associated with patient recovery.

In some variations, at least a portion of a robotic arm may be driven with one or more pulley arrangements (e.g., a pulley transmission, such as one including pulleys and cables that are wrapped around the pulleys). However, one drawback of pulley arrangements is that they tend to fail and/or lose performance due to cable loosening and/or cable breakage over the course of use. Furthermore, in some applications, it may be desired that pulley arrangements in a robotic arm are relatively compact, yet able to withstand high driving forces.

SUMMARY

In some variations, a pulley arrangement (e.g., a pulley transmission or other suitable pulley arrangement) may include a base pulley portion rotatable within a driving plane, an adjustable pulley portion coupled to the base pulley portion and rotatable relative to the base pulley portion within the driving plane, and a driving member including a first end coupled to the adjustable pulley portion, wherein at least a portion of the driving member is wrapped at least partially around the adjustable pulley portion. In some variations, the adjustable pulley portion may include a member that is coaxial with the base pulley portion. The adjustable pulley portion may be lockable in a selected rotational position relative to the base pulley portion, such that, for example, the pulley arrangement sets a selected level of tension in the driving member.

The adjustable pulley portion may, for example, be coupled to the base pulley portion via at least one opening in at least one of the adjustable pulley portion and the base pulley portion. In some variations, for example, the pulley arrangement may include at least one fastener passing through the at least one opening such that the fastener may be lockable in the at least one opening to thereby lock a rotational position of the adjustable pulley portion relative to the base pulley portion. For example, the at least one opening may be a slot, and the fastener may be lockable in a selected location within the slot to thereby lock a rotational position of the adjustable pulley portion relative to the base pulley portion. As another example, the at least one opening may be one of a plurality of openings in at least one of the adjustable pulley portion and the base pulley portion. Each opening may correspond to a respective rotational position of the adjustable pulley portion relative to the base pulley portion. The fastener may be lockable in a selected opening of the plurality of openings to thereby lock a rotational position of the adjustable pulley portion relative to the base pulley portion.

In some variations, the pulley arrangement may include a movable element engaged with the adjustable pulley portion, where the movable element is adjustable to thereby rotate the adjustable pulley portion relative to the base pulley portion. For example, the movable element may include a threaded member (e.g., fastener, threaded rod, etc.) with one end (e.g., including a hemi-spherical head or other suitable contact shape) that contacts the adjustable pulley portion. As the movable element's position is adjusted, the movable element may cause the adjustable pulley portion to move relative to the base pulley portion.

The pulley arrangement may, in some variations, include at least a second pulley, where the driving member wraps at least partially around the second pulley. The second pulley may, for example, be placed at a suitable distance from the base pulley portion. A second end of the driving member may be coupled to the second pulley. Additionally or alternatively, a second driving member may include an end coupled to the base pulley portion and another end coupled to the second pulley.

Generally, in some variations, a pulley arrangement may include a base pulley portion rotatable around an axis, an adjustable pulley portion coupled to the base pulley portion and movable in a first direction parallel to the axis; and a first sliding block engaged with the adjustable pulley portion. The first sliding block may be configured to move in a second direction different from the first direction, in response to compression of the adjustable pulley portion against the base pulley portion. The pulley arrangement may, in some variations, further include a driving member having a first end that is coupled to the first sliding block, and at least a portion of the driving member may be wrapped at least partially around the first sliding block and/or around the adjustable pulley portion. In some variations, the pulley arrangement may include one or more additional pulleys, such as an idler pulley, where at least one driving member wraps at least partially around the idler pulley.

The adjustable pulley portion and/or the first sliding block may include at least one sloped surface. For example, the sloped surface may include a helical surface. A sloped surface of the adjustable pulley portion may, for example, engage with the sliding block. Additionally or alternatively, a sloped surface of the sliding block may engage with the adjustable pulley portion.

In some variations, the pulley arrangement may include a second sliding block engaged with the adjustable pulley portion. A second end of the driving member, or an end of a second driving member, may be coupled to the second sliding block. The first and second sliding blocks may be configured to move circumferentially toward each other in response to compression of the adjustable pulley portion against the base pulley portion. Their movement may be at about equal rates in response to such compression (e.g., to provide bilaterally symmetrical tensioning) or different rates. In some variations, the first and second sliding blocks may be disposed in an arcuate gap defined at least in part by the adjustable pulley portion. In some variations, the first and/or second sliding blocks may be configured to move in an arcuate path, a linear path, or other suitable path in response to compression of the adjustable pulley portion against the base pulley portion.

The adjustable pulley portion may include a single member or multiple members engaged with one or more sliding blocks. For example, the adjustable pulley portion may include a first member engaged with the first sliding block and a second member engaged with the second sliding block, such that the first and second members are movable parallel to the axis around which the base pulley portion rotates. The axial position of the adjustable pulley portion relative to the base pulley portion may be lockable (e.g., with one or more fasteners, such as one or more fasteners coupling the adjustable pulley portion and the base pulley portion). In some variations, the adjustable pulley portion may be adjacent the base pulley portion, such as axially aligned. In some variations, the adjustable pulley may be disposed in a recess of the base pulley portion.

BRIEF DESCRIPTION OF THE DRAWINGS

FIGS. 12B and 12C are a sectional perspective view and a side view, respectively, of an adjusting pulley for adjusting tension in the pulley arrangement depicted in FIG. 12A.

FIGS. 13A-13C are schematic illustrations of a method of adjusting tension in a driving member with the adjusting pulley depicted in FIG. 12A.

FIG. 16B is a side view with detailed inset views of an adjusting pulley and an idler pulley in the exemplary variation of a pulley arrangement depicted in FIG. 16A. FIG. 16C is an exploded view of an exemplary adjusting pulley. FIG. 16D is an exploded view of an exemplary idler pulley.

DETAILED DESCRIPTION

Examples of various aspects and variations of the invention are described herein and illustrated in the accompanying drawings. The following description is not intended to limit the invention to these embodiments, but rather to enable a person skilled in the art to make and use this invention.

Robotic Arm Overview

Generally, a robotic or robotic-assisted surgical system (e.g., to enable a minimally-invasive surgical procedure) may include one or more robotic arms for manipulating surgical tools, such as during minimally-invasive surgery. As shown in FIG. 1A, a robotic arm 100 may include a plurality of links (e.g., 112a, 112b, 112c, 112d, etc.), and a plurality of actuated joints that enable relative movement between adjacent links. Additionally, a tool driver 130 may be coupled to a distal end of the robotic arm 100 and be configured to hold and actuate a surgical instrument 140 passing through a cannula 150. During use of the robotic arm 100 for a surgical procedure, a proximal end of the robotic arm 100 may be mounted or otherwise coupled to a structure (e.g., a surgical table, cart, wall, ceiling, etc.) at a mounting point near the patient during a surgical procedure. The surgical instrument 140 may pass through the cannula 150 through an incision or other entry point in the patient. Generally, the robotic arm 100 and/or tool driver 130 may be manipulated by a user in order to control the surgical instrument 140 within the patient (e.g., to perform surgical tasks, to position a camera, etc.). Other examples of a robotic surgical system are described in U.S. patent application Ser. No. 15/706,536 filed on Sep. 15, 2017 (U.S. Pat. No. 10,661,453) and titled "ROBOTIC ARMS", which is hereby incorporated in its entirety by this reference.

Figure 1B:
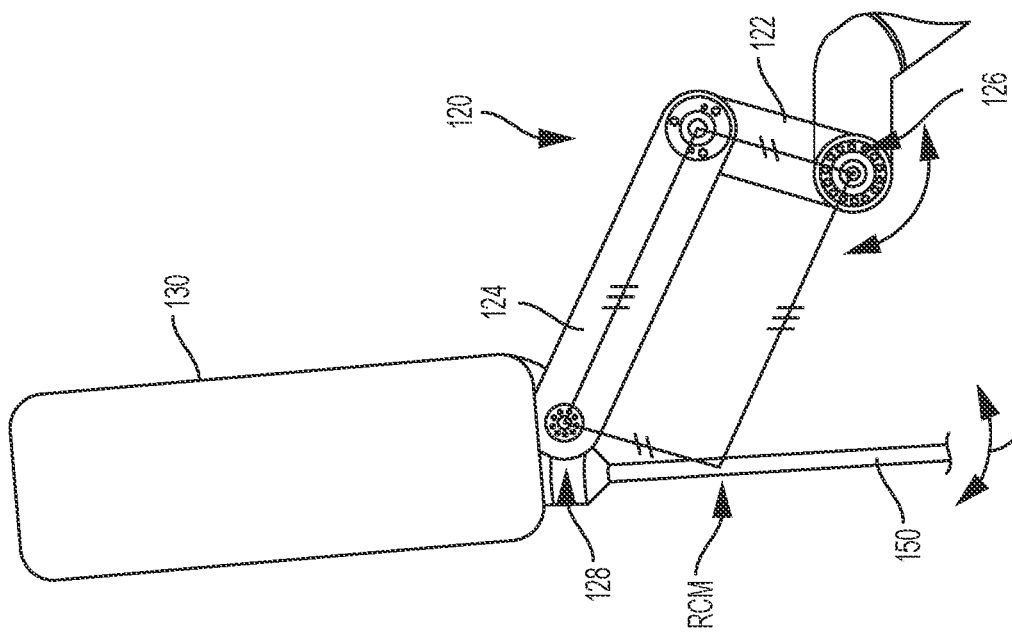
FIGS. 1A and 1B are illustrative schematics of an exemplary variation of a robotic arm, and an exemplary variation of a pitch assembly in a robotic arm, respectively.
Figure 1A:
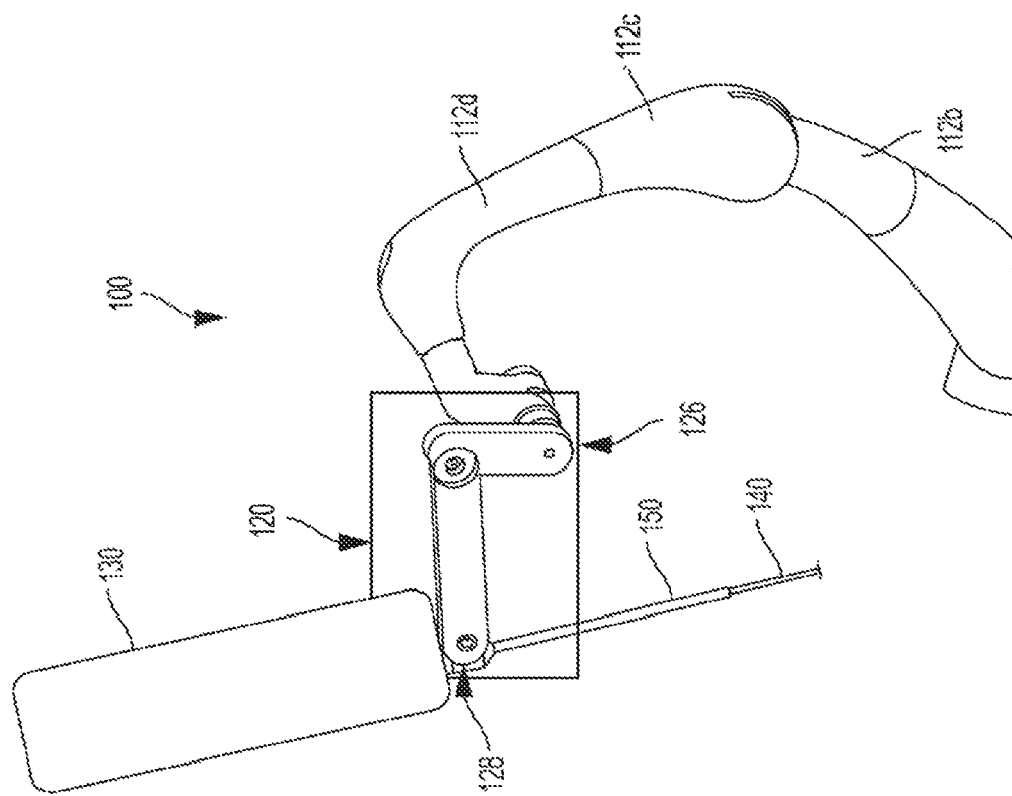

As shown in FIGS. 1A and 1B, the robotic arm 100 may further include a pitch assembly 120. The pitch assembly may include a first end 126 coupled to a portion of the robotic arm, and a distal end 128 which is coupled to the tool driver 130. As shown in FIG. 1B, the pitch assembly 120 may include at least a first pitch link 122 and a second pitch link 124 that actuate the cannula in a particular direction P around a particular axis, referred to herein as a pitch axis (e.g., pictured in FIG. 1B as passing through the page and coincident with, or near-coincident with, a mechanical remote center of motion, or RCM). For example, the first pitch link 122, the second pitch link 124, and the tool driver 130 may move as three links of a four-bar linkage (e.g., generally a parallelogram) that includes "ground" as a fourth link, constrained with a drive mechanism (such as a pulley arrangement or other suitable pulley transmission), in order to move the cannula around the pitch axis in a pitch direction P. Through this four-bar linkage motion, the pitch assembly 120 may replicate rotation of the first pitch link 122 around Axis A (pictured in FIGS. 1C and 1D) into rotation of the cannula around the pitch axis (e.g., around the mechanical RCM), where Axis A and the pitch axis are generally offset and parallel. In some variations, the pitch assembly may include any suitable number of links "n" to form an n-bar linkage. Accordingly, actuation of the first pitch link 122 around its first end 126 at Axis A may control a pitch movement of the cannula in the direction P. Although the pitch assembly 120 is primarily described herein as actuating the cannula around a pitch axis, it should be understood that in other variations or other orientations of the pitchy assembly 120, the links 122 and 124 may be configured to actuating the cannula around a particular axis in another direction (e.g., a yaw axis), depending on, for example, how the assembly 120 is oriented, etc.

Figure 1D:
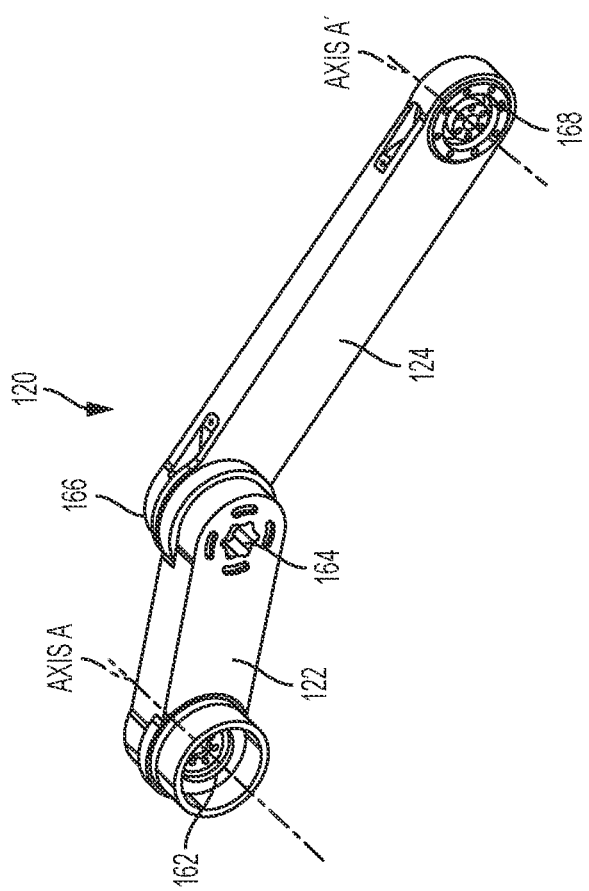
FIGS. 1C and 1D are perspective detailed views of an exemplary variation of a pitch assembly with a pulley arrangement.
Figure 1C:
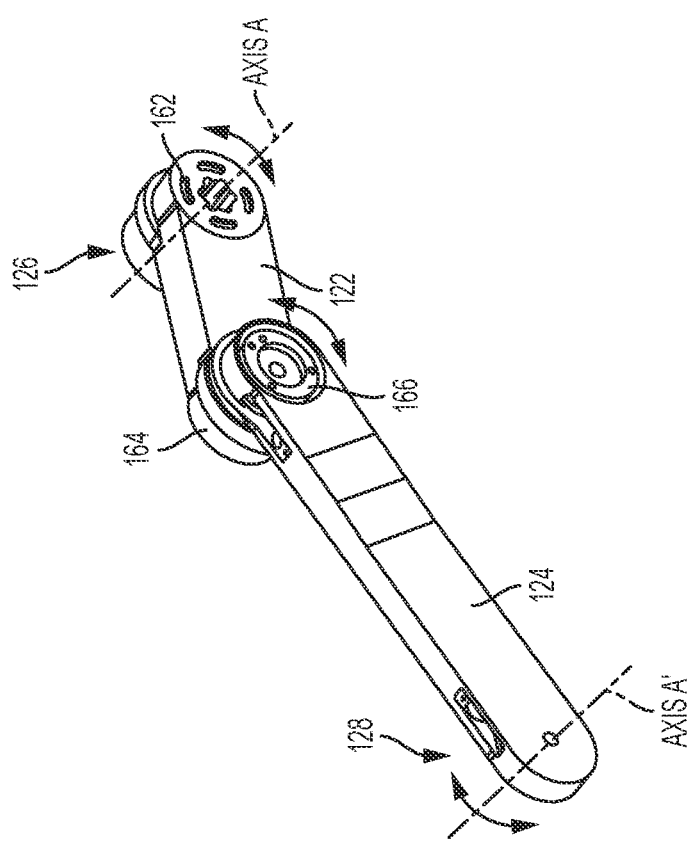

The pitch assembly 120 may be configured to operate the surgical instrument 140 about the RCM with increased ease, speed, and flexibility. Additionally, the pitch assembly 120 may be configured to collapse into a compact pose or configuration. For example, as shown in FIGS. 1C and 1D, the first pitch link 122 may be shorter than the second pitch link 124, such that the first pitch link 122 may rotate relative to the second pitch link 124 without physical interference and allow the pitch assembly 120 to collapse or fold down against itself. Such a configuration can, for example, be useful for storage, transport, and/or increased range of motion of the robotic arm 100, such as during a surgical procedure.

The pitch linkage assembly 120 may include a series of pulleys and a series of driving members (e.g., metal bands, cables, chains, other suitable driving members, etc.) connecting the pulleys that facilitate four-bar linkage movement. For example, with reference to FIGS. 1C and 1D, the first pitch link 122 may be coupled to an actuator (not shown) that drives rotation of first pitch link 122 around Axis A, while the second pitch link 124 may be rotationally coupled to the tool driver. The first pitch link 122 may include a first pulley 162 coupled to the actuator and located generally at a proximal point of first pitch link 122, within an internal space of first pitch link 122. The first pitch link 122 may also include a second pulley 164 located generally at a distal point of the first pitch link 122, within the internal space of the first pitch link 122. The second pulley 164 may be rigidly fixed to a proximal point of the second pitch link 124.

Additionally, the second pitch link 124 may include a third pulley 166 located generally at a proximal point of the second pitch link 124, mounted on and rigidly fixed to a shaft of the first pitch link 122 that extends into an internal volume of the second pitch link 124, such that when the first pitch link 122 rotates, the third pulley 166 rotates correspondingly. The second pitch link 124 may also include a fourth pulley 168 located generally at a distal point of the second pitch link 124, within the internal space of the second pitch link 124. The tool driver may be rotationally coupled to the distal point of the second pitch link 124 and thus constrained to move when the fourth pulley 168 rotates around Axis A'.

At least one driving member (not shown) may wrap around the first and second pulleys 162 and 164 such that when an actuator drives rotation of the first pitch link 122 at its first end 126 around Axis A, the orientation of the second pitch link 124 remains fixed relative to the orientation of the housing of the actuator. Similarly, at least one driving member (not shown) may wrap around the third and fourth pulleys 166 and 168 such that when the second pitch link 124 rotates, the tool driver orientation remains fixed relative to the orientation of the first pitch link 122. In sum, rotation of the first pitch link 122 around Axis A may be transformed through the system of pitch links, pulleys, and bands into rotation of the tool driver around Axis A' via four-bar linkage movement (e.g., in a parallelogram), and thus drives movement of the cannula around the pitch axis as described above (e.g., around a mechanical RCM). In some variations, the at least one driving member may include one or more cables, belts, and/or other suitable driving members or driving members.

Figure 15A:
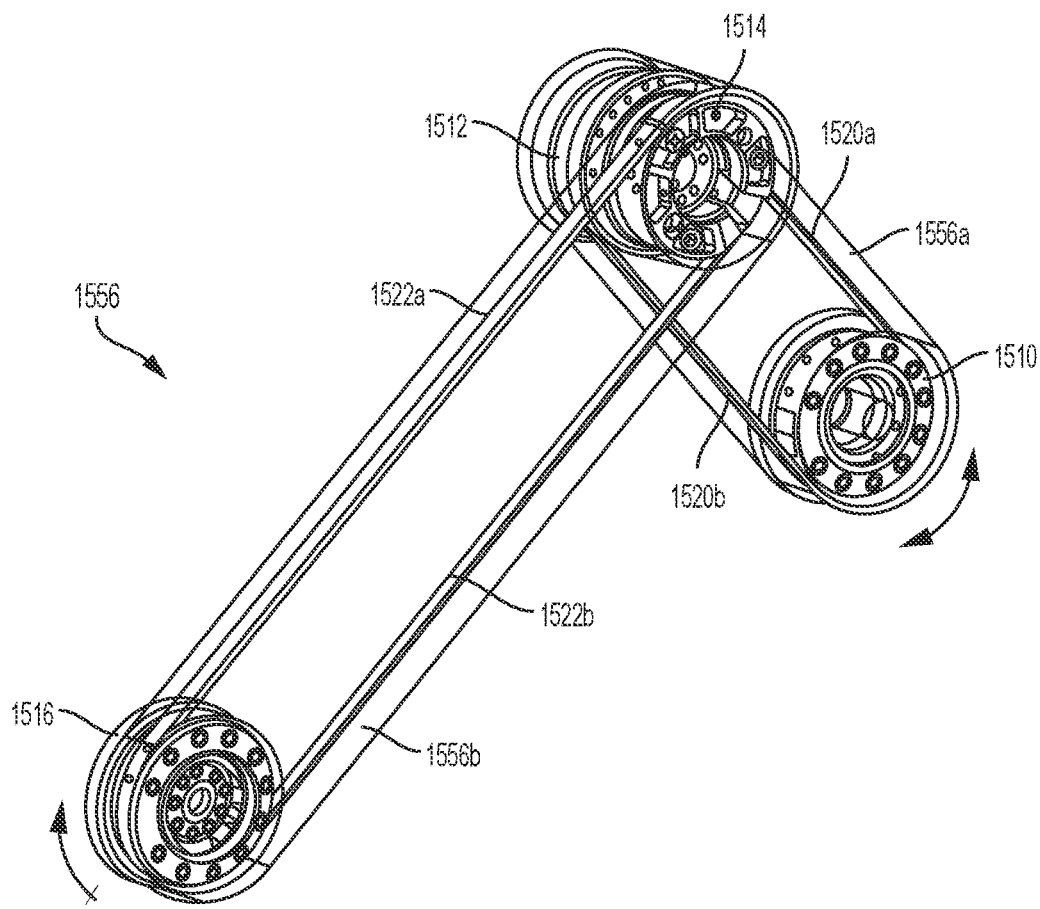
FIGS. 15A and 15B are perspective and top views, respectively, of an exemplary variation of a pitch link assembly incorporating one or more pulley arrangements.
Figure 15B:
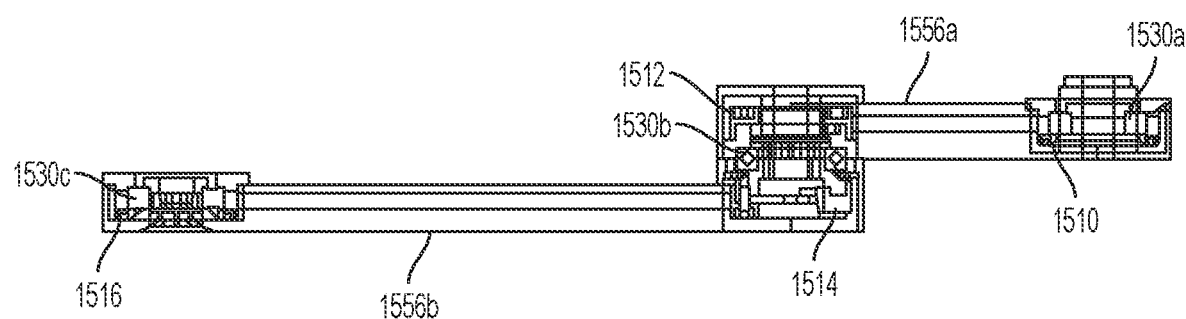

For example, in the variation shown in FIGS. 15A and 15B, the pitch assembly 1556 includes a first pitch link 1556a, a second pitch link 1556b, and a set of pulleys and driving members (e.g., bands) configured to constrain motion of the pitch assembly in a manner similar to the variation described above with reference to FIGS. 1C and 1D. In this variation, the first pitch link 1556a has a terminating pulley 1510 configured to couple to the housing of a joint module actuator or other chassis of the robotic arm, and the first pitch link 1556a is rigidly fixed to an adjustable pulley 1514 located within the second pitch link 1556b. The second pitch link 1556b is rigidly fixed to an adjustable pulley 1512 and further includes a terminating pulley 1516 configured to couple to a tool driver. Rotational movement of the various components may be facilitated by bearings, such as a bearing 1530a facilitating relative movement of the rest of the robotic arm and the first pitch link 1530a, a bearing 1530b facilitating relative movement between the first and second pitch links 1556a and 1556b, and a bearing 1530c facilitating relative movement of the second pitch link 1556b and the tool driver.

A pair of driving members (e.g., belts or bands) 1520a and 1520b may extend between terminating pulley 1510 and adjustable pulley 1512, with first ends terminating rigidly at the terminating pulley 1510 (e.g., coupled by welding or other suitable connection) and second ends coupled to the adjustable pulley 1512 (e.g., through welding or other suitable connection). Similarly, a pair of driving members (e.g., belts) 1522a and 1522b extend between terminating pulley 1516 and adjustable pulley 1514, with first ends terminating rigidly at the terminating pulley 1516 and second ends coupled to the adjustable pulley 1514. As a result of the driving member and pulley system, when the first pitch link 1556a is rotated around terminating pulley 1510, the second pitch link 1556b translates in-plane without rotating (e.g., staying parallel to its previous orientation), while the terminating pulley 1516 moves in an arc about the remote center of motion.

In some variations, a pulley arrangement (e.g., pulley transmission or other suitable pulley arrangement) in a robotic arm (e.g., a pitch assembly) may include one or more attachment configurations for coupling a driving member to a pulley with increased resistance against shear forces that otherwise may tend to decouple the driving member from the pulley, cause any multiple layers of a driving member (e.g., a stack of layers, as described in further detail below) to slip relative to one another, and/or cause loss of tension in the driving member, and in a manner that occupies less overall volume and/or occupies less surface area of the pulley. Additionally or alternatively, the pulley arrangement may include one or more tensioning mechanisms for adjusting tension in the driving member. For example, the driving member may be tensioned to a predetermined tension during manufacturing, assembly, and/or calibration of the pitch assembly, to help guard against and/or compensate for fatigue loads that otherwise may tend to cause the driving member to slacken and result in poorer operational performance in the pulley arrangement. Various examples of attachment configurations and tensioning mechanisms are described in further detail below.

Driving Member and Attachment

Generally, when a pulley arrangement is used, significant driving forces may be applied to the one or more driving members that wrap at least partially around a pulley and/or at the attachment point of the driving member to the pulley. For example, as the pulley arrangement is operated (e.g., at least one pulley rotates), one or more driving members may be loaded in tension. As another example, as the pulley arrangement is operated, one or more attachment points for a driving member (where a terminating end of the driving member is coupled to a pulley) may loaded with a shear force (e.g., relating to tensile load in the driving member). If such forces are significant enough, they may cause the pulley arrangement to fail in one or more different ways. For example, the driving member may break if driving forces exceed its tensile strength, or an attachment point may fail if shear forces exceed the shear strength of the joint between the terminating end of the driving member and the pulley. In some variations, a driving member may be wrapped more than once around the entire circumference of the pulley, which may help shield the attachment point from experiencing the full load of forces during operation of the pulley arrangement. However, even in these variations the driving member and its attachment point to the pulley are still subject to failure due to the driving forces in the pulley arrangement, and the increased bulk of the pulley arrangement due to extra wrapping may be undesirable in some applications.

Furthermore, in some applications, it may be advantageous to attach a driving member to a pulley using as little surface area of the pulley as possible, in order to increase the amount of useful angular travel of the pulley (e.g., less "dead" wrap or "static" wrap of the driving member) and thus enable the pulley arrangement (and, for example, a linkage assembly driven by the pulley arrangement) to have a greater range of motion.

Below are exemplary variations of driving members, and exemplary variations of pulley-driving member attachment arrangements that may be secure, compact, and/or occupy less surface area of the pulley without sacrificing attachment strength of the driving member to the pulley. It should be understand that although at least some of the systems and methods for attachment are primarily described herein as coupling two ends of one driving member to a pulley, the same systems and methods for attachment may be used to secure ends of two separate driving members to a pulley (i.e., one end of a first driving member and one end of a second driving member to the pulley).

Driving Members

Figure 2A:
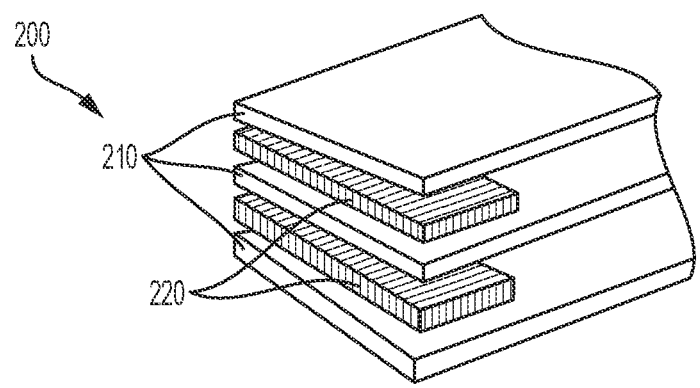
FIG. 2A is an illustrative schematic of an exemplary variation of a multi-layered driving member in a pulley arrangement.

As shown in FIG. 2A, in some variations, a driving member 200 for a pulley arrangement may include a plurality of layers of one or more materials arranged in a stack, such that a load (e.g., tensile driving force) applied to the driving member is distributed across the multiple layers. Generally, with multiple layers of materials load-sharing in such a manner, the driving member as a whole may withstand a greater applied load before failing (e.g., due to cyclic loading around the pulley, and/or other factors). The layers of the driving member may be joined at least a termination end of the driving member. Additionally or alternatively, layers of the driving member may joined along the length, or part of the length, of the driving member in lamination.

Figure 2B:
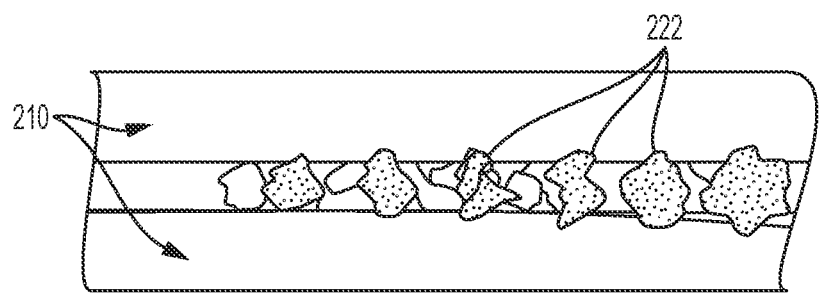
FIG. 2B is a detailed view of a shear substrate in an exemplary variation of a driving member.

In some variations, as shown in FIG. 2A, at least some of the layers of the driving member may include a first material 210 and a second material 220 that interleaves with the primary material. The first material 210 may function to bear tensile loads applied to the driving member and may include, for example, metal, plastic, carbon fiber, etc. The second material 220 may function as a shear substrate that increases shear strength at an attachment point. The second material 220 may include, for example, an adhesive solution (e.g., a cyanoacrylate adhesive or other suitable liquid adhesive, a double-sided structural adhesive, or suitable epoxy, etc.). As another example, as shown in FIG. 2B, the second material 220 may additionally or alternatively include particles 222 (e.g., diamond particles, silicon carbide particles, etc.) suitable for deforming the lamination of the first material 210, such that they provide a physical connection between layers of the first material 210. The particles 222 may be mixed among a carrier solution of adhesive and/or non-adhesive materials, and the particles may be distributed and at least partially embedded into the adjoining surfaces of the first material 210 such that the particles are mechanically locked into the first material 210. In some variations, the particles 222 may generally have a diameter that is up to about half the thickness of the adjacent layer(s) of the first material 210. For example, in one variation, if a layer of first material 210 includes a band about 0.002 inches thick, the particles 222 may be up to about 25 microns in diameter. Such a physical connection transfers mechanical forces between the layers of the first material 210 in response to applied shear forces, thereby increasing the overall stiffness of the joint. Various other suitable mixtures of adhesive and/or non-adhesive solutions may be mixed with particles and cured prior to or during lamination of the first material 210. Additionally or alternatively, the second material 220 may include a suitable filler material (e.g., aluminum-silicon, copper or copper alloy, nickel alloy, etc.) for brazing layers of the first material 210 together.

Dimensions and material choice for a multi-layered driving member may be selected depending on the needs for the specific application. For example, the thickness of a multi-layered driving member may depend on various factors such as the anticipated loads that the driving member is expected to withstand, the type or types of materials in each layer, the radius of the pulley, the thickness of each layer, the number of layers, and the width of the driving member. As one example, generally, total thickness of the driving member in a pulley arrangement for a robotic arm may range between about 0.2 millimeters and about 1 millimeter, between about 0.4 millimeters and about 0.8 millimeters, or between about 0.50 millimeters and about 0.7 millimeters.

In one exemplary variation, a multi-layered driving member may include about six layers of metal (e.g., 301-HY stainless steel), where each metal layer may be about 0.05 millimeters thick. The metal layers, at a termination end of the driving member, may be interleaved with a mixture of cyanoacrylate adhesive and diamond particles. The diamond particles may have a diameter of about 0.5 microns or 0.6 microns.

In other variations, the driving member may include any suitable number of layers (e.g., at least two, three, four, five or more layers). Furthermore, although exemplary multi-layered driving members are described above, the variations of attachment methods described below may be used in combination with any suitable kind of driving member (e.g., single layer of a belt or band) made of any suitable kind of material.

Compressive Attachment

In some variations, a terminating end of a driving member may be attached to a pulley in the pulley arrangement via at least a compressive arrangement. A compressive arrangement may provide good resistance against fatigue over repeated operation of the pulley arrangement, such that the driving member is less likely to loosen over time. Additionally, a compressive arrangement may avoid weaknesses that may be introduced in the driving member material by other attachment methods using welding, which may cause undesirable heat stresses near the attachment point of the driving member to the pulley. Furthermore, when used in combination with fasteners or pins passing through holes in the driving member, a compressive arrangement may exert a compressive force that provides good frictional contact to transfer loads, thereby reducing or eliminating stress concentration around the holes in the driving member that would otherwise contribute to failure of the driving member around the attachment point.

Generally, a compressive arrangement for attaching a driving member to a pulley may include compressing at least a portion of the driving member (e.g., a terminating end thereof) against the pulley. For example, at least a portion of the driving member and the pulley may be sandwiched between two opposing surfaces. The opposing surfaces may, for example, be aligned and/or compressed toward each other with a fastener such as a threaded member (e.g., bolt or screw). Such a fastener may be secured with a nut (e.g., locknut, jam nut, etc.). As further illustrated by the examples described below, at least one of the opposing surfaces may include, for example, an additional compressive component such as a washer or clamp plate that increases surface area and friction against the pulley and/or driving member, and thus increases shear strength of the attachment joint when the compressive arrangement is tightened and secured with the fastener. As another example, at least a portion of the driving member and the pulley may be compressed against the pulley with a wedge or other suitable compressive element. Other variations of compressive arrangements for attaching a driving member to a pulley or other surface are described herein.

Figure 3B:
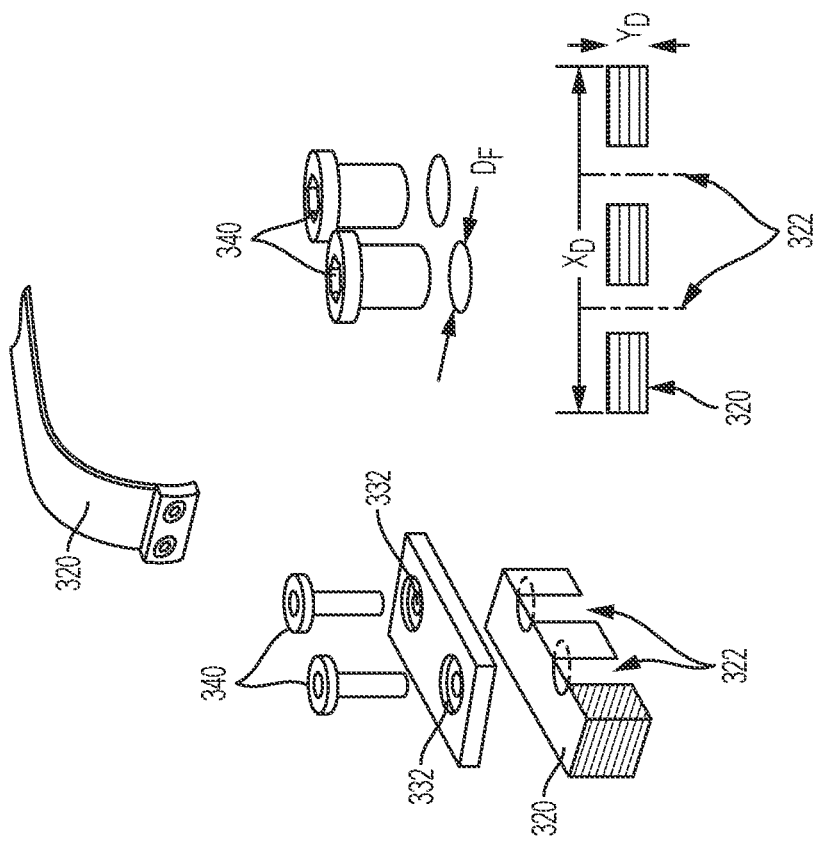
FIGS. 3A and 3B are a perspective view and exploded views, respectively, of an exemplary variation of a driving member attachment to a pulley.
Figure 3A:
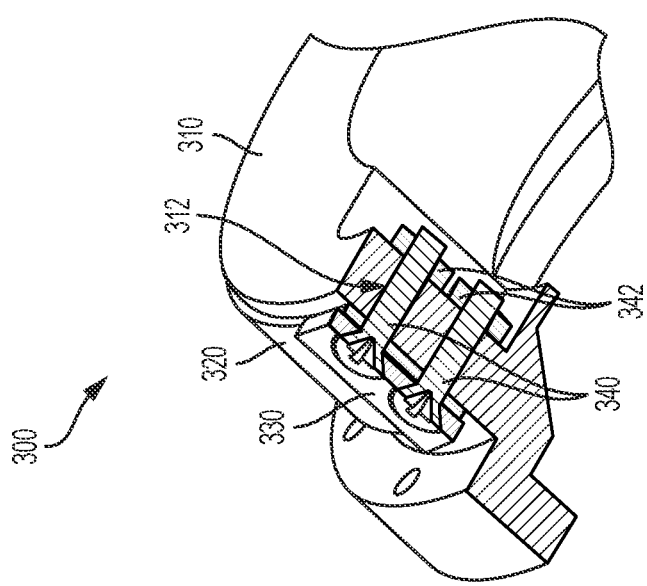

In one exemplary variation, as shown in FIGS. 3A and 3B, a compressive arrangement 300 for coupling a driving member to a pulley may include a pulley 310, a driving member 320, and a clamp 330. A suitable shear substrate (e.g., as described above with reference to FIG. 2B) such as a cyanoacrylate adhesive may be disposed between the pulley 310 and the driving member 320 and/or between the driving member 320 and the clamp 330. The shear substrate between the pulley 310 and the driving member 320 may be different or substantially similar to the shear substrate between the driving member 320 and the clamp 330. As shown in FIG. 3A, at least one fastener 340 (e.g., threaded screw) may pass through a hole 332 in the clamp, a hole 322 in the driving member, and a hole 312 in the pulley.

The clamp 330 may include a plate with holes 332 formed therein (e.g., by machining, 3D printing, casting, etc.). Although the clamp 330 is shown in FIGS. 3A and 3B as a generally flat or level plate with two holes 332, it should be understood that in other variations, the clamp 330 may be arcuate (e.g., arcuate with a similar radius of curvature as the pulley 310) and include any suitable number holes, such as two, three, four, five, six, or more holes in any suitable pattern to accommodate any suitable number of fasteners 340. At least some of the holes 332 may, in some variations, be countersunk for receiving the heads of the fasteners 340 such that the fasteners 340 lie generally flush with the surface of the clamp 330. The clamp 330 may include a material that is softer than the material of the driving member so as not to deform the driving member when the clamp 330 is tightened onto the driving member. The clamp may, in some variations, have a thickness generally the same as the thickness of the driving member, but may alternatively have any suitable thickness. In some variations, the circumferential length of the clamp 330 relative to the width of the driving member may be between about 1:1.5 and about 1:3, or about 1:2.

In some variations, the one or more holes 312 in the pulley 310 may be threaded to receive a threaded fastener 340 such that one or more fasteners 340 may sandwich and compress the clamp 330 and the driving member 320 against the pulley 310 in a compressive arrangement, as the fasteners 340 are advanced into the holes 312. Additionally or alternatively, a nut 342 (e.g., jam nut, lock nut, etc.) may engage with a distal end of a fastener 340 to secure the clamped assembly together. A threadlocker adhesive (e.g., LOCTITE) may, in some variations, be applied to the threads of the fastener 340 to further secure the clamped assembly against fatigue and loosening.

As shown in FIG. 3A, the compressive arrangement 300 may include a plurality of fasteners 340 (e.g., at least two, three, four, five, etc.) to secure the compressive arrangement of the clamp 330, driving member 320, and pulley 310. A desired particular arrangement of fasteners (size, number, etc.) for attaching the driving member 320 to the pulley without a weld may be assessed based on the geometry and/or material properties of the driving member and fasteners, and their effect on stress experienced at the interface between the driving member and fasteners.

For example, the mathematical expressions below may be used to determine desired fastener diameter based at least in part on characterizations of shear stresses of the driving member and fasteners, and on known geometries illustrated in FIG. 3B and other known material properties. Shear stress $\sigma_F$ of the fasteners in the compressive arrangement may be expressed as shown in Equation (1) below:

$$\sigma_F = \frac{P_F}{A_F} = \frac{P_F}{N_F \pi \left(\frac{D_F}{2}\right)^2} \tag{1}$$

where $P_F$=force at the shear location of the fasteners, $A_F$=area of the fasteners at the shear location, $N_F$=number of fasteners, $D_F$=diameter of each fastener, and $\sigma_F$=ultimate tensile strength (UTS) of the fastener material.

Additionally, shear stress $\sigma_D$ of the driving member may be expressed at shown in Equation (2) below:

$$\sigma_D = \frac{P_D}{A_D} = \frac{P_D}{N_D Y_D (X_D - N_F D_F)} \quad (2)$$

where $P_D$=force at the shear location of the driving member, $A_D$=area of the driving member at the shear location, $N_D$=number of layers in the driving member at the shear location, $Y_D$=thickness of each layer in the driving member, $X_D$=width of each layer in the driving member, $N_F$=number of fasteners, $D_F$=diameter of each fastener, and $\sigma_D$=ultimate tensile strength (UTS) of the driving member layer material.

Assuming that, at the interface between the driving member and fasteners, shear force $P_F$ acting on the fasteners by the driving member is equal to the shear force $P_D$ acting on the driving member by the fasteners, Equations (3)-(6) can be developed:

$$P_F = P_D \quad (3)$$

$$\sigma_F A_F = \sigma_D A_D \quad (4)$$

$$\sigma_F N_F \pi \left(\frac{D_F}{2}\right)^2 = \sigma_D N_D Y_D (X_D - N_F D_F) \quad (5)$$

$$\frac{\sigma_F N_F \pi}{4} D_F^2 + \sigma_D N_D Y_D N_F D_F - \sigma_D N_D Y_D X_D = 0 \quad (6)$$

Using Equation (6), the desired diameter $D_F$ of each fastener can be determined using the quadratic formula $$D_F = \frac{-b \pm \sqrt{b^2 - 4ac}}{2a} \quad (7)$$

where $$a = \frac{\sigma_F N_F \pi}{4} \quad (8)$$

$$b = \sigma_D N_D Y_D N_F \quad (9)$$

$$c = \sigma_D N_D Y_D X_D \quad (10)$$

Equations (7)-(10) provide for one positive value and one negative value, with the positive value being the desired fastener diameter based on the known or predetermined geometries and material characteristics of the driving member and fasteners.

In other words, once materials and particular geometries of the compressive arrangement are selected and known, Equations (1)-(10) may be applied to determine a desired fastener diameter for the compressive arrangement. Furthermore, in some variations, the compressive arrangement may include fastener sizes that incorporate additional safety factors (e.g., 1.5×, 1.75×, 2×, etc.) applied to the determined fastener diameter. Such safety factors may be incorporated in order to increase confidence that the attachment of the driving member to the pulley (via the compressive arrangement) will not fail during expected use of the pulley arrangement. It should be understood that although Equations (1)-(10) are described with reference to the compressive arrangement 300, these equations are not necessarily solely applicable to the compressive arrangement 300, and may be modified to determine desired parameters of other attachment arrangements described herein.

In another exemplary variation, as shown in FIGS. 4A-4D, a compressive arrangement 400 for coupling a driving member to a pulley may include a pulley 410, a driving member 420 with overlapping first and second ends 422 and 424, respectively, and at least two opposing surfaces secured by at least one fastener 434 and nut 436 for clamping the overlapping ends of the driving member 420 to the pulley 410. As shown best in FIG. 4C, the opposing surfaces in the compressive arrangement 400 may include a first washer 430 and a second washer 432 arranged on opposing sides of the pulley 410 and driving member ends 422 and 424. At least one of the washers 430 and 432 may be a wave spring washer or the like, which imparts a spring pressure when compressed in the compressive arrangement, so as to increase the likelihood that the compressive arrangement provides a positive compressive force at the attachment location throughout the life of the pulley arrangement.

Generally, the fastener 434 (e.g., a threaded member such as a bolt or screw) may pass through the first washer 430, the pulley 410, through the first and second ends 422 of the driving member 420, through the second washer 432, and through the nut 436. In some variations, the diameter of the fastener may be less than or equal to about half the width of the driving member 420. The nut 436, which is threadingly engaged with the fastener 434, may be tightened to clamp and secure the pulley 410 and driving member ends together between the first washer 430 and the second washer 432. The nut 436 may be a locknut or jam nut with threadlocker, etc. in order to help secure the nut's location on the fastener 434 and maintain compressive force.

Figure 4A:
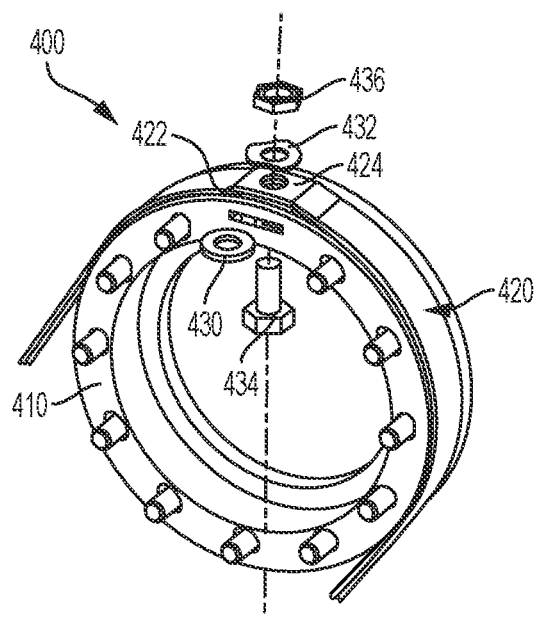
FIGS. 4A-4D are perspective, cross-sectional, side, and perspective detailed views, respectively, of an exemplary variation of a driving member attachment to a pulley.
Figure 4B:
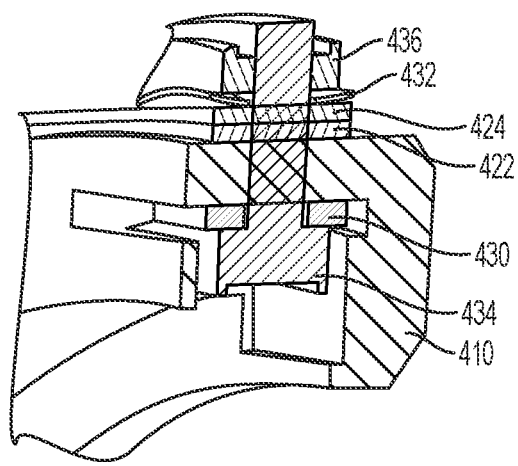
Figure 4C:
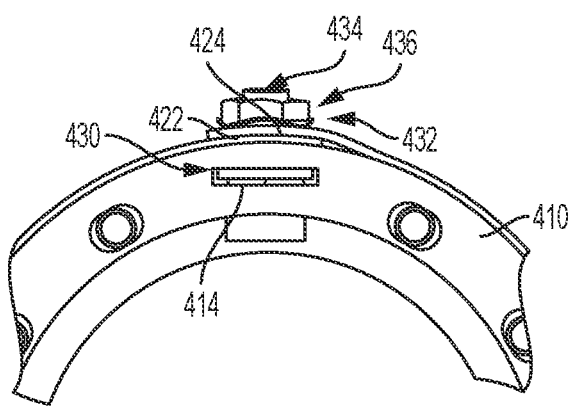
Figure 4D:
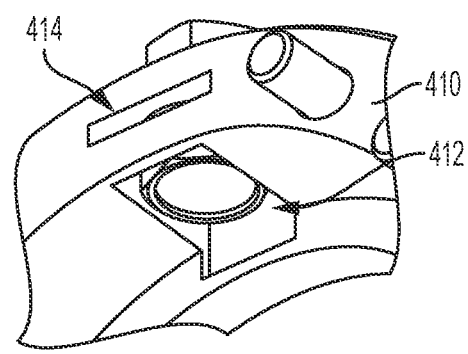

In some variations, as shown in FIG. 4B, the pulley 410 may include a recess to receive the head of the fastener (or alternatively, the nut 436). Additionally or alternatively, as shown in FIG. 4D, the pulley 410 may define a flat surface 412 against which the head of the fastener 434 may abut such that the fastener does not rotate (e.g., while or after the compressive arrangement is tightened). During assembly, the washer 430 may be inserted through a slot 414 in the pulley 410 to be positioned in the path of the fastener 434.

Figure 5B:
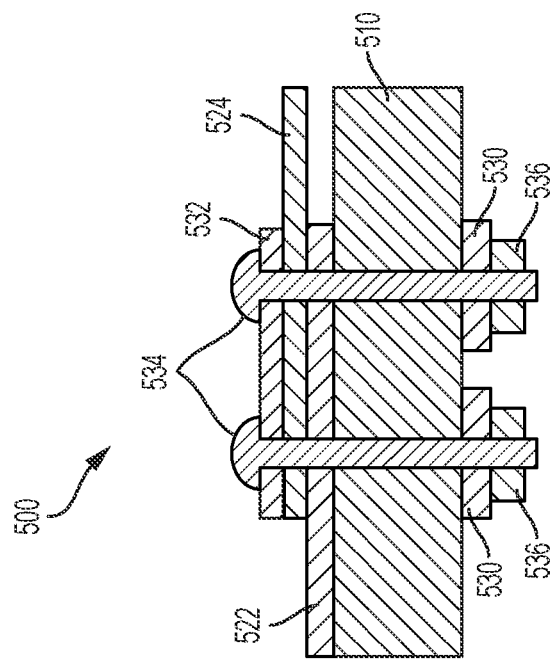
FIGS. 5A and 5B are perspective and side views, respectively, of an exemplary variation of a driving member attachment to a pulley.
Figure 5A:
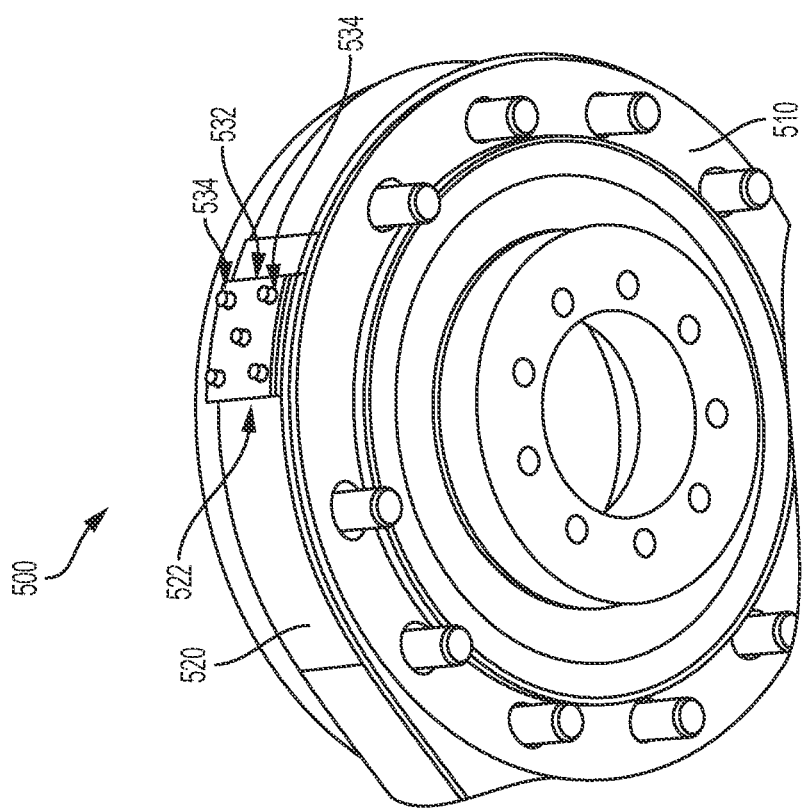

In another exemplary variation, as shown in FIGS. 5A and 5B, a compressive arrangement 500 for coupling a driving member to a pulley may include a pulley 510, a driving member 520 with overlapping first and second ends 522 and 524, respectively, and at least two opposing surfaces secured by one or more fasteners 534 and nuts 536 for clamping the overlapping ends of the driving member 520 to the pulley 510. As shown best in FIG. 5B, the opposing surfaces in the compressive arrangement 500 may include a washer 530 and a clamp 532 arranged on opposing sides of the pulley 510 and driving member ends 522 and 524. The clamp 532 may, for example, be similar to the clamp 330 described above with reference to FIGS. 3A and 3B.

Generally, the fasteners 534 may pass through the clamp 532, through the second and first ends 524 and 522, respectively, through the pulley 510, through the washer 530, and through the nut 536. In some variations, the diameter of a fastener 534 may be less than or equal to about half the width of the driving member 520. In some variations, the fasteners 534 may be threaded (e.g., bolt or screw) and threadingly engage with holes in the pulley 510 and/or the nuts 536. In other variations, one or more of the fasteners 534 may be press-fit into the pulley 510 to thereby secure the driving member 520 against the pulley 510.

As shown in FIG. 5A, the compressive arrangement 500 may be secured with more fasteners having smaller diameters instead of fewer fasteners having larger diameters. For example, the compressive arrangement 500 is depicted as including five fasteners passing through a set of respective five holes in the clamp 534 and driving member ends 522 and 544. More numerous smaller holes, instead of fewer larger holes, may reduce stress concentration around the holes that are more prone to failure (e.g., in the event the shear strength of the attachment joint is overcome by the driving forces of the pulley arrangement).

In another exemplary variation, as shown in FIGS. 6A-6D, a compressive arrangement 600 for coupling a driving member to a pulley may include a pulley 610 having at least one projection 616, and a driving member 620 with first and second ends 622 and 624 where at least one of the first and second ends 622 and 624 wraps at least partially around a projection 616 on the pulley 610. In the variation shown in FIG. 6C, each of the driving member ends 622 and 624 may wrap around a respective projection 616. The compressive arrangement 600 may further include at least two opposing surfaces secured by at least one fastener 634 and nut 636 for clamping the driving member ends 622 and 624 onto the projections 616 of the pulley 610. As shown best in FIG. 6C, the opposing surfaces in the compressive arrangement 600 may include a first clamp 640 disposed on a first side (e.g., inner side) of the projections 616 and a second clamp 642 disposed on a second side (e.g., outer side) of the projections 616. The clamps 640 and 642 may, for example, be similar to the clamp 330 described above with reference to FIGS. 3A and 3B. The first clamp 640 may be configured to compress parts of the driving member ends 622 and 624 against the first side of the projections 616. The second clamp 642 may be configured to compress parts of the driving member ends 622 and 624 against the second side of the projections 616. Generally the fastener 634 may pass through the clamps 640 and 642 and nut 636 to compress and secure the driving member ends around the projections 616 of the pulley.

Additionally or alternatively, the opposing surfaces in the compressive arrangement 600 may include a first washer 630 and/or a second washer 632. At least one of the washers 630 and 632 may be a wave spring washer or the like, which imparts a spring pressure when compressed in the compressive arrangement, so as to increase the likelihood that the compressive arrangement provides a positive compressive force at the attachment location throughout the life of the pulley arrangement.

Additionally or alternatively, the opposing surfaces clamping the driving member ends 622 and 624 onto the projections 616 of the pulley 610 may be on the fastener 634 itself. For example, the head of the fastener 634 may be shaped (e.g., machined) to match the curvature of the pulley 610, and be large enough to provide enough compressive force on the driving member ends 622 and 624.

Figure 6A:
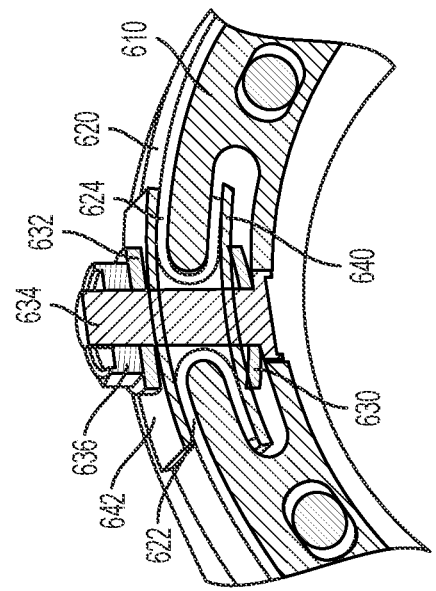
FIGS. 6A-6D are perspective, cross-sectional, side, and detailed views, respectively, of an exemplary variation of a driving member attachment to a pulley.
Figure 6B:
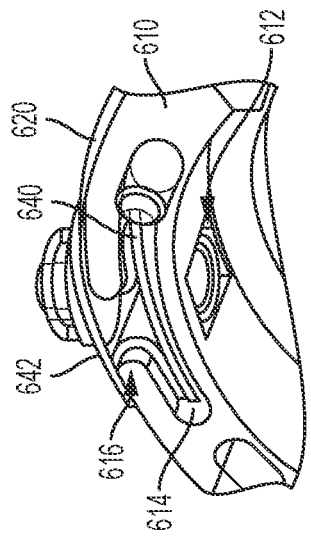
Figure 6C:
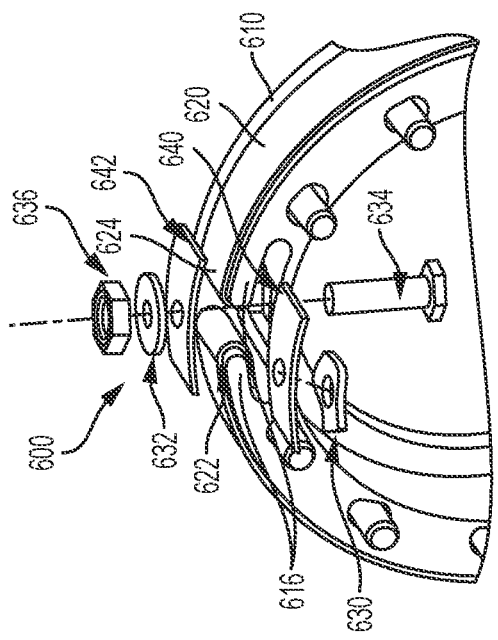
Figure 6D:
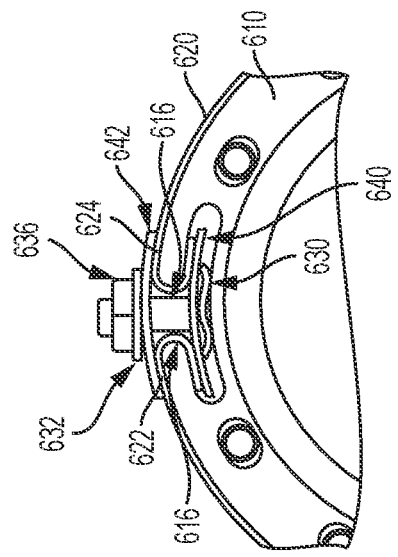

In some variations, similar to that described above with reference to FIG. 4B, the pulley 610 may include a recess to receive the head of the fastener (or alternatively, the nut 636). Additionally or alternatively, as shown in FIG. 6D, the pulley 610 may define a flat surface 612 against which the head of the fastener 634 may abut such that the fastener does not rotate (e.g., while or after the compressive arrangement is tightened). During assembly, the washer 630 and/or clamp 640 may be inserted through a slot 614 in the pulley 610 to be positioned in the path of the fastener 634.

Figure 7:
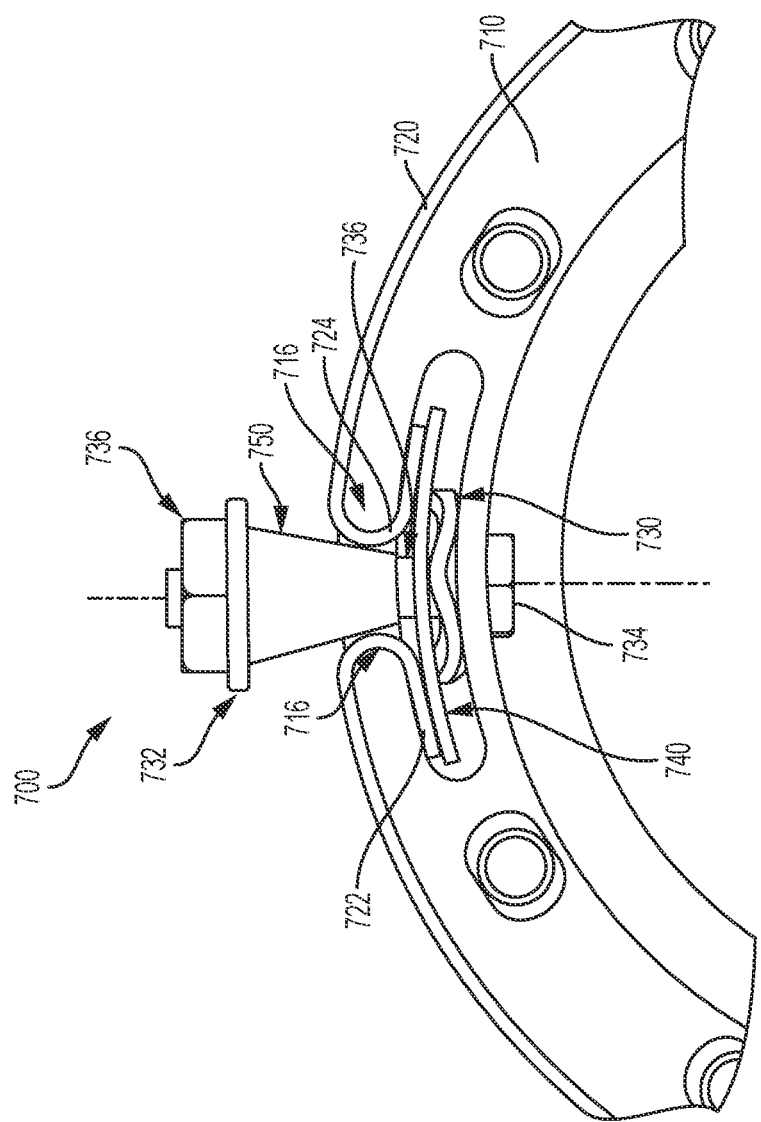
FIG. 7 is a side view of an exemplary variation of a driving member attachment to a pulley.

In another exemplary variation, as shown in FIG. 7, a compressive arrangement 700 is similar to compressive arrangement 600, except as described below. The compressive arrangement 700 for coupling a driving member to a pulley may include a pulley 710 having at least one projection 716, and a driving member 720 with first and second ends 722 and 724 where at least one of the first and second ends 722 and 724 wraps at least partially around a projection 716 on the pulley 710. In the variation shown in FIG. 7, each of the driving member ends 722 and 724 may wrap around a respective projection 716. The compressive arrangement 700 may further include a wedge 750 configured to compress the driving member ends 722 against the projections 716. For example, the wedge 750 may be generally prismatic with tapered edges such that the wedge narrows in width along a radial direction. Alternatively, the wedge 750 may be conical or frustoconical, etc. The wedge may be made of a high-friction material such as rubber or other suitable material. A fastener 734, secured by nut 736, may pass through a lumen of the wedge 750 between the projections 716 such that as the fastener is tightened, the wedge 750 is urged radially and its increasing width at the points of contact with the driving member ends 722 and 724 causes the wedge 750 to further compress the driving member ends 722 and 724 against the projections 716 in the pulley.

The compressive arrangement 700 may further include at least one clamp 740 disposed on an inner side of the projections 716 to help secure the ends of the driving member to the pulley. The claim 740 may, for example, be similar to the clamp 330 described above with reference to FIGS. 3A and 3B. Additionally or alternatively, the compressive arrangement 700 may include a first washer 730 and/or a second washer 732. At least one of the washers 730 and 732 may be a wave spring washer or the like, which imparts a spring pressure when compressed in the compressive arrangement, so as to increase the likelihood that the compressive arrangement provides a positive compressive force at the attachment location throughout the life of the pulley arrangement.

Figure 9:
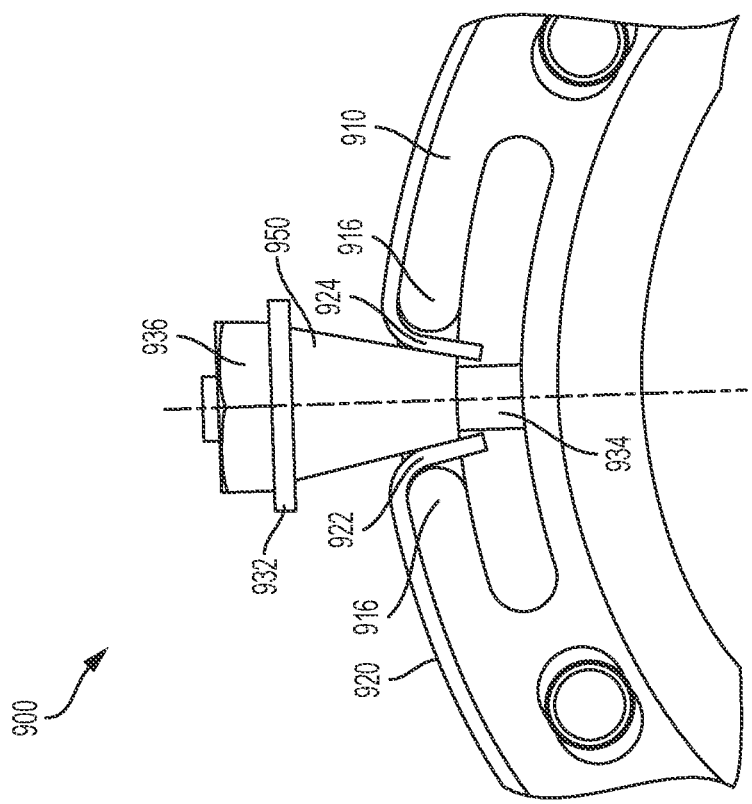
FIG. 9 is a side view of an exemplary variation of a driving member attachment to a pulley.
Figure 8:
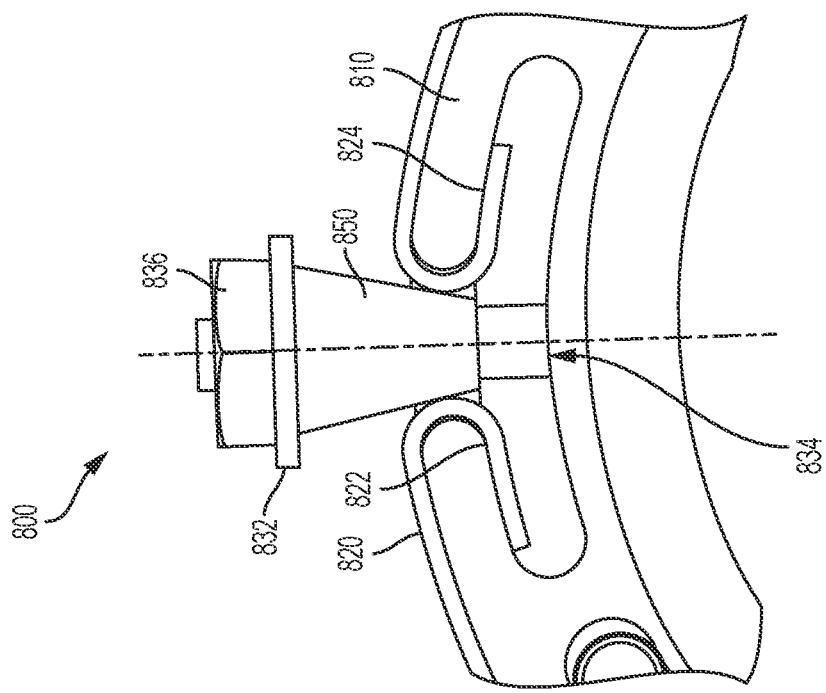
FIG. 8 is a side view of an exemplary variation of a driving member attachment to a pulley.

In another exemplary variation, as shown in FIG. 8, a compressive arrangement 800 is similar to compressive arrangement 700, except as described below. For example, the compressive arrangement 800 may include a pulley 810 having at least one projection 816, and a driving member 820 with first and second ends 822 and 824, where at least one of the first and second ends wraps at least partially around a projection on the pulley 810. The compressive arrangement 800 may further include a wedge 850 such as that similar to wedge 750 described above with reference to FIG. 7. A threaded fastener 834, secured at one end with a nut 836, may pass through a lumen of the wedge 850 and into a threaded hole of the pulley 810. As the fastener is tightened (e.g., nut 936 and washer 832 are advanced against the wedge 850), the wedge 850 is urged radially and its increasing width at the points of contact with the driving member ends 822 and 824 causes the wedge 850 to further compress the driving member ends 822 and 824 against the projections in the pulley 810. Another exemplary variation of a compressive arrangement 900 is shown in FIG. 9. Compressive arrangement 900 is similar to compressive arrangement 800, with elements numbered similar to those in compressive arrangement 800, except that the ends 922 and 924 of the driving member wrap less around the projections 916 compared to ends 822 and 824 of the driving member as shown in FIG. 8.

Figure 10A:
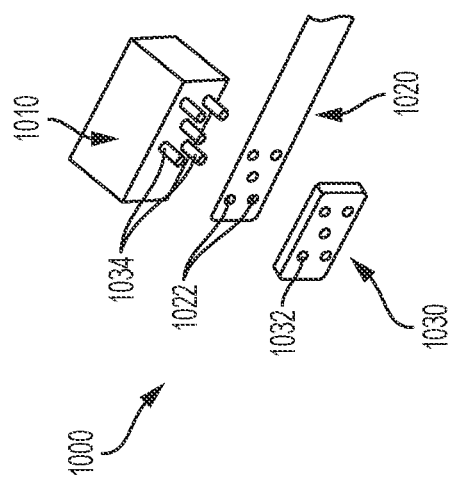
FIG. 10A is an exploded view of an exemplary variation of a driving member attachment to a pulley.
Figure 10D:
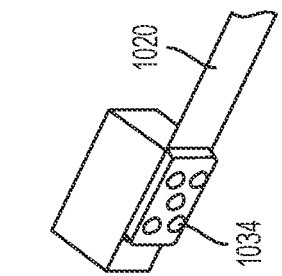
FIGS. 10B-10D are schematic illustrations of a method for assembling the driving member attachment depicted in FIG. 10A.

In another exemplary variation, as shown in FIG. 10A, a compressive arrangement 1000 may include a block 1010 (e.g., part of a pulley or a component coupled to a pulley) having one or more deformable pins 1034, a driving member 1020, and a clamp 1030. The pins 1034 may, for example, be machined out of the block 1010, and/or may be pins that are inserted into respective holes in the block 1010 (e.g., via press-fit, etc.). The pins may be received through holes 1022 in the driving member 1020 and holes 1032 in the clamp 1030 in the arrangement of FIG. 10B. As shown in FIG. 10B, the block 1010 and clamp 1030 may have mateable surfaces that sandwich and compress the driving member on opposite sides of the driving member.

Figure 10C:
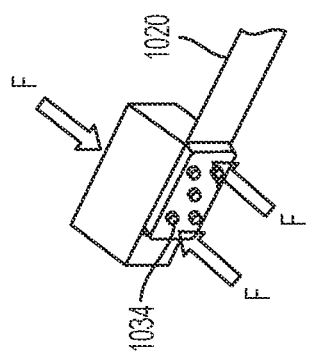
Figure 10B:
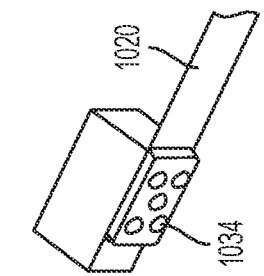

As shown in FIG. 10C, a compressive force F may be applied to the block and clamp assembly, so as to deform at least one of the pins 1034 into a rivet or rivet-like shape that secures the driving member 1020 against the block 1010. For example, the compressive force F may be applied via a clamp with one or more recesses, each recess receiving a respective distal end of a pin 1034 such that the recess molds or otherwise forms the distal end of the pin 1034 into a rivet or rivet-like shape. The compressive force F may be applied to multiple (two or more, or all) pins 1034 simultaneously, or may be applied to each pin sequentially.

Furthermore, although the block 1010 and clamp 1032 are depicted in FIG. 10A as having flat mateable surfaces, it should be understood that in other variations, they may have angled surfaces, curved surfaces (e.g., arcuate with the same radius of curvature), or other suitable mating surfaces. Particular dimensions, number, materials, etc. of pins on the block may, in some variations, be selected based on an analysis of parameters such as those utilized in Equations 1-10 as described above.

In some exemplary variations, the block 1010 and pins 1034 may made of stainless steel (e.g., 304SST) or carbon steel, with or without additional alloying elements (e.g., high strength low allow steel, which may include, for example, additional alloying elements such as manganese, copper, titanium, vanadium, niobium, etc. to the carbon or any suitable material. The clamp may be made of annealed steel (e.g., AISI 1010) or other suitable material that may be relatively soft (e.g., to provide sufficient contact for improving friction). As shown in FIG. 10A, the block 1010 may include five pins, each with a diameter of about 1 mm, and may be arranged in a bilaterally symmetrical pattern such as with four pins at four corners of a rectangle measuring about 4 mm×about 3 mm and a fifth pin in the center of the rectangle. The forming operation on the pins to deform the pins into rivets or rivet-like shapes may be formed one at a time under a compressive force of about 1500 N. In these variations, each forming operation may achieve, for example, around 300N of clamping force to secure the driving member 1032 to the block 1010.

Brazed Attachment

In some variations, a terminating end of a driving member may be attached to a pulley in the pulley arrangement via at least brazing. The driving member may include multiple layers of a metal material that are coupled via brazing with a braze alloy filler material, and the driving member may further be coupled to a pulley or other component via brazing with the same or different braze alloy filler material. The resulting brazed joint may be as strong as or stronger than the strength of the full cross-section of all metal strips.

Figure 11:
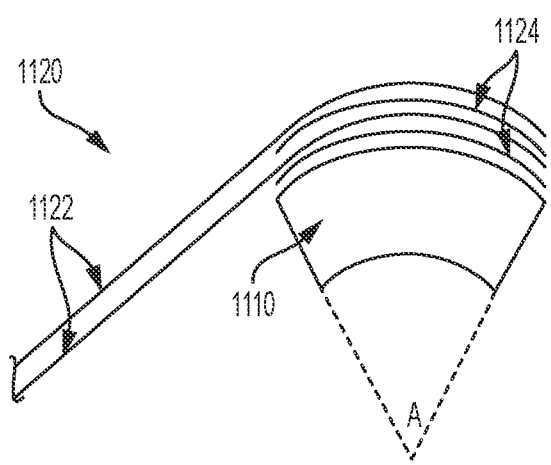
FIG. 11 is a schematic illustration of an exemplary variation of a brazed driving member attachment to a pulley.

For example, as shown in FIG. 11, a multi-layer driving member 1120 (e.g., similar to that described above with reference to FIGS. 2A and 2B) may be brazed to a metal block 1110. The metal block 1110 may be portion of a pulley or a component coupled to a pulley. The multi-layer driving member may be brazed to an arcuate segment of the block sweeping an angle A, where angle A may be, for example, between about 10 degrees and 25 degrees, or between about 15 degrees and about 20 degrees. The multi-layer driving member 1120 may include at least one metal belt layers 1122 and at least one filler layer 1124. The metal belt layers 1122 may include stainless steel or other suitable material. The filler layers 1124 may include a suitable braze alloy such as aluminum-silicon, copper or copper alloy, nickel alloy, etc. Although FIG. 11 depicts a driving member 1120 with two metal layers and two filler layers 1124, it should be understood that any suitable number of metal belt layers and/or filler layers may be included.

In some exemplary variations, the block 1010 is an arcuate segment made of stainless steel (e.g., 304SST) or carbon steel, with or without additional alloying elements. The multi-layer driving member may include multiple metal strips (e.g., 301-HY stainless steel) that are brazed to one another with a filler material. Additionally, the multi-layer driving member may be brazed along the arc length of the block 1010 that sweeps about 17.5 degrees. In one example, the driving member may include up to about five layers of metal belt material each with a thickness of about 0.13 mm and a width of about 6 mm. As another example, the driving member may include up to about twelve layers of metal belt material each with a thickness of about 0.05 mmm and a width of about 6 mm. These examples may result in a brazed joint having a shear strength of about 6800 N.

Tensioning Mechanisms

Described below are variations of tensioning mechanisms in pulley arrangements that enable tensioning of driving members attached to one or more pulleys. Generally, appropriately tensioned driving members help facilitate the rotational motion within a pulley arrangement (e.g., within a pitch assembly such as pitch assembly 120 described above with reference to FIGS. 1C and 1D).

In some variations, the one or more driving members may be tensioned to a predetermined tension level at least during manufacturing, assembly, and/or calibration of the pitch assembly. Additionally or alternatively, the one or more driving members may be monitored and re-tensioned during and over the course of use of the robotic arm. For example, throughout operation of a pulley arrangement, fatigue loads applied to the pulley arrangement over an extended period of time may cause the one or more driving members to slacken and lose their tension, thereby resulting in poorer performance in the pulley arrangement (e.g., less positional accuracy, slower actuating response times, etc.). Thus, periodic or intermittent tensioning of the one or more driving members may be desired in order to maintain performance. Additionally or alternatively, at least a portion of the pulley assembly may be swappable to be replaced with appropriately-tensioned pulley assembly parts, such as part of regular maintenance.

Accordingly, in some variations, a pulley arrangement (such as one included in the pitch assembly 120 as shown in FIGS. 1C and 1D in a robotic arm) may further include a tensioning mechanism. For example, the tensioning mechanism can include at least one tensioner pulley located in plane with the first and second pulleys 162 and 164 and corresponding one or more bands, and at least one tensioner pulley located in plane with the third and fourth pulleys 166 and 168 and corresponding one or more bands. The in-plane locations of the tensioning pulleys may be adjusted and set (e.g., with fasteners) in order to calibrate the tension of the bands. However, the pitch assembly 120 may include a turnbuckle, or any suitable tensioning assembly. Other exemplary variations of tensioning mechanisms, such as those described below, may be incorporated in the pulley arrangement.

Split Pulleys

Figure 12A:
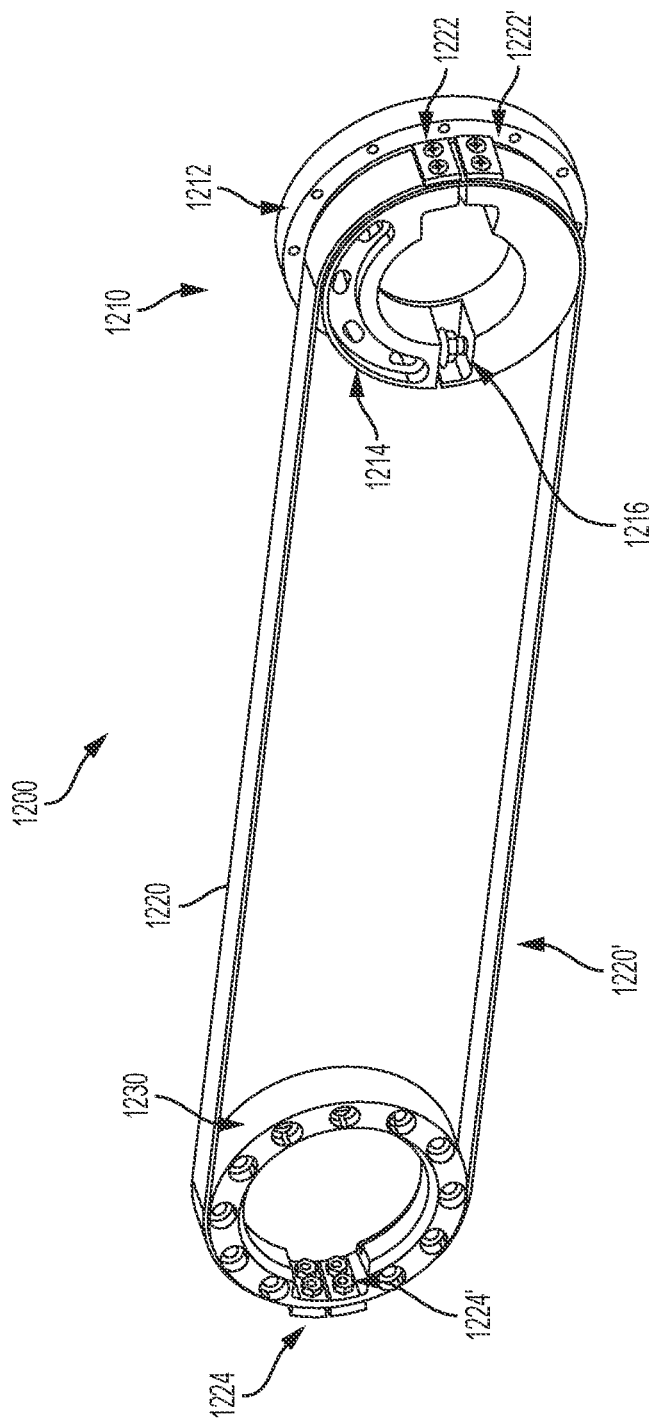
FIG. 12A is a perspective view of an exemplary variation of a pulley arrangement enabling tensioning of a driving member.

In some variations, as shown in FIG. 12A, a pulley arrangement 1200 may include an adjusting pulley 1210 and an idler pulley 1230 that are connected via a first driving member 1220 and a second driving member 1220'. A first end 1222 of a first driving member 1220 may couple to and wrap at least partially around the adjusting pulley 1210, and a second end 1224 of the first driving member 1220 may couple to and wrap at least partially around the idler pulley 1230. Similarly, a first end 1222' of a second driving member 1220' may couple to and wrap at least partially around the adjusting pulley 1210, and a second end 1224' of the second driving member 1220' may couple to and wrap at least partially around the idler pulley 1230. Alternatively, the adjusting pulley 1210 and the idler pulley 1230 may be connected via a single driving member 1220, with a first end 1222 of the driving member 1220 coupled to and wrapping at least partially around the adjusting pulley 1210, a body portion of the driving member 1220 wrapping around the idler pulley 1230, and a second end 1224 of the driving member 1220 coupled to and wrapping at least partially around the adjusting pulley 1210. Any suitable attachment mechanism or arrangement, including any of the driving member attachment variations described herein, may be used to couple an end of one or both driving members to the adjusting pulley and/or idler pulley. The pulley arrangements with adjusting pulleys described below may, for example, be used to adjust tension in the driving member in those variations in which the idler pulley may be a fixed distance from the base pulley portion (though in some variations the idler pulley position may be adjustable in distance from the base pulley portion, such as to further adjust tension in the driving member or members).

In some variations, a pulley arrangement may include an adjusting pulley for adjusting tension in the pulley arrangement, the adjusting pulley including a base pulley portion rotatable within a driving plane, and an adjustable pulley portion coupled to the base pulley portion. The adjustable pulley portion may be rotatable relative to the base pulley portion within the driving plane. The pulley arrangement may further include a driving member comprising a first end coupled to the adjustable pulley portion, wherein at least a portion of the driving member is wrapped at least partially around the adjustable pulley portion. Examples of these variations are shown in FIGS. 12A-12C and FIGS. 14A-14B.

As shown in FIGS. 12A-12C, a pulley arrangement may include a base pulley portion 1212, an adjustable pulley portion 1214 rotatable relative to the base pulley portion 1212, and at least one driving member 1220 having a first end 1222 coupled to and wrapping at least partially around the adjustable pulley portion 1214. Another driving member end 1222' (of the same driving member 1220 or another driving member 1220') may be coupled to the base pulley portion 1212 and wrap at least partially around the base pulley portion 1212. The base pulley portion and the adjustable pulley portion may be generally circular or arcuate. For example, the base pulley portion and/or the adjustable pulley portion may be ring-like or partial ring-like as shown in FIGS. 12B and 12C. Alternatively, the base pulley portion and/or the adjustable pulley portion may be in the shape of a disc or partial disc with an arcuate edge.

As shown in FIG. 12A, the base pulley portion 1212 may include a mounting region 1212a and a driving region 1212b. The mounting region 1212a may be configured to mount the base pulley portion 1212 to a surrounding structure (e.g., an arm segment such as a pitch link in a robotic arm), such as with fasteners. The driving region 1212b may include an arcuate surface configured to engage with the driving member 1220. For example, the driving member 1220 may wrap at least partially around the arcuate surface of the driving region 1212b. In some variations, the driving region 1212b may be a surface that is at least about the width of the driving member 1220.

Like the base pulley portion 1212, the adjustable pulley portion 1214 may include a mounting region 1214a and a driving region 1214b. The mounting region 1214a may be configured to couple the adjustable pulley portion 1214 to the base pulley portion 1212. For example, as shown in FIG. 12B, one or more fasteners 1213 (e.g., screws, bolts, etc.) may pass through openings 1215 and into threaded holes (not shown) in the base pulley portion 1212, in order to axially constrain the adjustable pulley portion 1214 relative to the base pulley portion 1212. The driving region 1214b may include an arcuate surface configured to engage with the driving member 1220. For example, the driving member 1220 may wrap at least partially around the arcuate surface of the driving region 1214b. In some variations, the driving region 1214b may be a surface that is at least about the width of the driving member 1220. Furthermore, as shown for example in FIG. 12C, one end of the driving member 1220 may be coupled (e.g., with any of the attachment arrangements described herein, or in any suitable manner) to the driving region 1214b at point A of the adjustable pulley portion 1214.

The driving region 1214b of the adjustable pulley and the driving region 1212b of the base pulley portion may, in combination, approximate at least part of a circle. For example, the driving region 1214b and the driving region 1212b may be nearly semi-circular. As another example, the driving region 1212b may sweep a major arc while the driving region 1214b sweeps a minor arc, or vice versa. As yet another example, both the driving region 1214b and the driving region 1212b may sweep a minor arc. The adjustable pulley portion 1214 and the driving region 1212b of the base pulley portion may be generally coaxial and have approximately the same radius of curvature, such that a driving member 1220 and/or a driving member 1220' may rotate with the pulley arrangement at a consistent rate of travel.

The adjustable pulley portion 1214 may be configured to rotate relative to the base pulley portion 1212. As described above, one end of the driving member 1220 may be coupled to and wrapped at least partially around the adjustable pulley portion 1214, and another end of the driving member 1220 may be coupled to a ground location (e.g., idler pulley 1230 as shown in FIG. 12A or point B on the base pulley portion 1212 as shown in FIG. 12C). In such an arrangement, the adjustable pulley portion 1214 may be radially constrained to rotate relative to the base pulley portion via a kinematic constraint between the pulley portions and the tension of the belt.

Furthermore, rotation of the adjustable pulley portion 1214 in a particular direction relative to the base pulley portion 1212 may tension the driving member 1220. In some variations, pulley arrangement may include a movable element engaged with the adjustable pulley portion, where the movable element may be adjustable to thereby rotate the adjustable pulley portion 1214 relative to the base pulley portion 1212. For example, the movable element may include a threaded member 1216 (e.g., carriage bolt or other suitable fastener). One end of the threaded member 1216 may be coupled to the base pulley portion 1212, and another end of the threaded member 1216 may be in contact with the adjustable pulley portion 1214. Advancement and/or retraction of the threaded member 1216 may cause displacement of the adjustable pulley portion 1214.

FIGS. 13A-13C depict various exemplary rotational positions of the adjustable pulley portion 1214 corresponding to different levels of tension in the driving member 1220. In FIG. 13A, the adjustable pulley portion 1214 is in a rotational position corresponding to a relatively low amount of tension in the driving member. The threaded member 1216 is in a retracted state. In this rotational position, the fasteners 1213 that axially couple the adjustable pulley portion 1214 to the base pulley portion 1212 are generally located at a first end (e.g., right end, as depicted in FIG. 13A) of the slot openings 1215.

In FIG. 13B, the adjustable pulley portion 1214 is in a rotational position corresponding to a moderate amount of tension in the driving member. The threaded member 1216 is advanced upwards (in the orientation shown in FIG. 13B) by a moderate distance to thereby rotationally displace the adjustable pulley portion 1214 in a clockwise direction. In this adjusted rotational position, the adjustable pulley portion 1214 causes the end of the driving member 1220 attached at "A" to be closer to the end of the driving member attached at "B," which increases tension in the driving member. In this rotational position, the fasteners 1213 are generally located in the middle of the slot openings 1215.

In FIG. 13C, the adjustable pulley portion 1214 is in a rotational position corresponding to a relatively high amount of tension in the driving member. The threaded member 1216 is advanced further than in FIG. 13B to thereby further displace the adjustable pulley portion 1214 in a clockwise direction. In this adjusted rotational position, the adjustable pulley portion 1214 causes the end of the driving member attached at "A" to be even closer to (e.g., adjacent to) the end of the driving member attached at "B," which further increases tension in the driving member compared to the arrangement of FIG. 13B. In this rotational position, the fasteners 1213 are generally located at a second end of the slot openings 121.

The three levels of tension are depicted in FIGS. 13A-13C as illustrative examples. It should be understood that the possible range of selectable tension in the driving member may be continuous and include levels of tension between those depicted in FIGS. 13A-13C. Additionally, in some variations, levels of tension may be attainable beyond the low and high levels of tension depicted in FIGS. 13A and 13C. For example, the adjustable pulley portion 1214 may be positioned at a more counter-clockwise position than in FIG. 13A, which corresponds to an even lower level of tension in the driving member. As another example, such as if the driving regions 1212*b* and 1214*b* (of the base pulley portion and adjustable pulley portion, respectively) may be overlapped, the adjustable pulley portion 1214 may be positioned at a more clockwise position than FIG. 13C, which enables the driving member ends at "A" and "B" to overlap and result in an even higher level of tension in the driving member compared to FIG. 13C. Furthermore, in some variations, the possible range of selectable tension may be discrete (e.g., via detents in the openings 1215, etc.).

As shown in FIGS. 13A-13C, in some variations, the threaded member 1216 may include a hemi-spherical head configured to contact the adjustable pulley portion at a tangential point as the rotational position of the adjustable pulley portion 1214. By contacting the adjustable pulley portion 1214 only at a single point as the rotational position of the adjustable pulley portion varies, the hemi-spherical head of the threaded member 1216 may help ensure proper kinematic coupling between the base pulley portion, the adjustment pulley portion, and the threaded member 1216. In some variations, the hemi-spherical head of the threaded member 1216 may have a single radius of curvature such that the rate of linear travel of the threaded member 1216 corresponds to a consistent rate of rotational travel of the adjustable pulley portion, and therefore results in a consistent amount of tensioning per unit of travel of the threaded member 1216. In other words, the ratio between a unit of linear travel of the threaded member 1216 and a unit of rotational travel of the adjustable pulley portion may be generally constant while the head of the threaded member 1216 and the adjustable pulley portion are in contact.

Furthermore, in some variations, as shown in FIGS. 13A-13C, the threaded member 1216 may include one or more features that may be engaged to advance and/or retract the threaded member 1216 relative to the base pulley portion. For example, the threaded member 1216 may include along its length one or more flat surfaces that may be grasped with a clamp, wrench, or other suitable tool from a lateral or radial approach relative to the length of the threaded member (e.g., since the head of the threaded member 1216 may be at least partially obstructed by the adjustable pulley portion). Such a tool may be used to grasp and turn the threaded member 1216 to advance and/or retract the threaded member 1216. Alternatively, an underside of the head of the threaded member, or other suitable portion of the threaded member, may be engaged to advance and/or retract the threaded member and rotate the adjustable pulley portion 1214.

The adjustable pulley portion may be lockable in a selected rotational position relative to the base pulley portion, thereby setting a selected tension level in the driving member. For example, once the adjustable pulley portion's rotational position is selected, the fasteners 1213 may be tightened in their locations in the slot openings 1215 to thereby lock the adjustable pulley portion in the selected rotational position (and lock the selected tension level in the driving member). Thus, by moving the adjustable pulley portion and locking its rotational position, the tension of the driving member maybe adjusted and locked during assembly of the pulley arrangement (e.g., as part of the manufacturing process), during a calibration procedure, and/or during maintenance, etc.

Figure 14A:
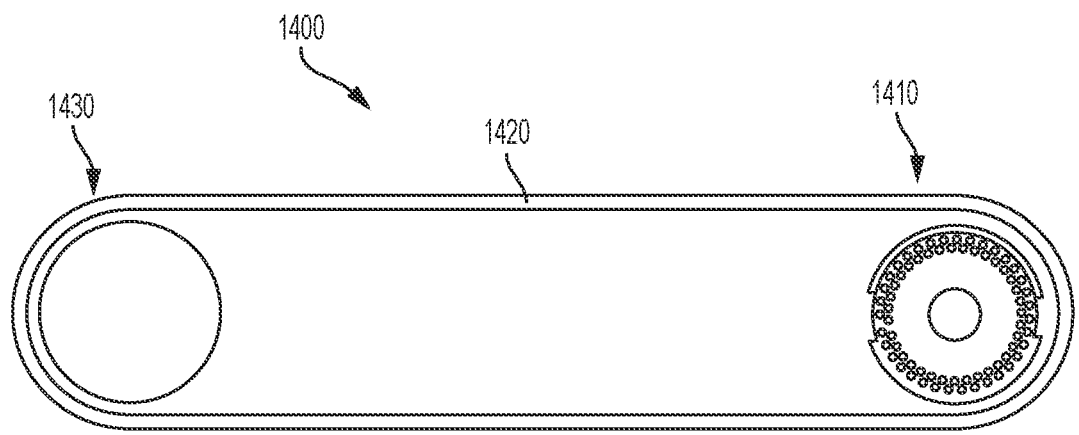
FIG. 14A is a side view of an exemplary variation of a pulley arrangement enabling tensioning of a driving member.
Figure 14B:
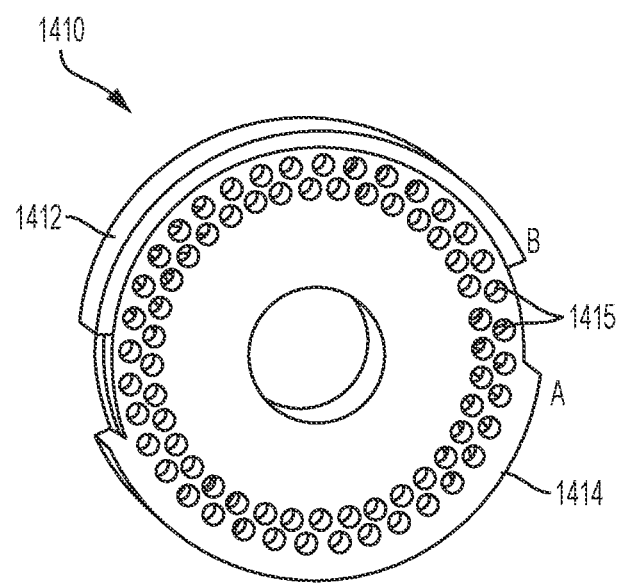
FIG. 14B is a side view of an adjusting pulley in the pulley arrangement depicted in FIG. 14A.

Another variation of a pulley arrangement 1400 is shown in FIGS. 14A and 14B. The pulley arrangement 1400 is similar to pulley arrangement 1200 shown in FIG. 12A except as described below, with similar numbering of elements. For example, the pulley arrangement 1400 may include an adjusting pulley 1410 and an idler pulley 1430 that are connected via at least one driving member 1420. Any suitable attachment mechanism or arrangement, including any of the driving member attachment variations described herein, may be used to couple an end of one or both driving members to the adjusting pulley and/or idler pulley. The pulley arrangements with adjusting pulleys described below may, for example, be used to adjust tension in the driving member in those variations in which the idler pulley may be a fixed distance from the base pulley portion (though in some variations the idler pulley position may be adjustable in distance from the base pulley portion, such as to further adjust tension in the driving member or members).

As shown in FIG. 16D, the idler pulley 1630 may include a base 1632 and a flange 1634 axially aligned with and coupled to the base 1632. The base 1632 may include a driving region around which at least part of the driving member 1620 and/or the driving member 1620' may be wrapped. Ends of the driving members 1620 and/or 1620' may be coupled to the base 1632 via anchor blocks 1622 engaged with base 1632, or in any suitable manner (e.g., attachment methods described herein). The flange 1634 may, for example, provide a wall that guides the driving members along the driving region of the base 1632 and helps prevent the driving members from slipping out of plane with the pulley arrangement.

The pulley arrangement 1400 may include an adjusting pulley 1410 as shown in FIG. 14B. The adjusting pulley 1410 may include a base pulley portion 1412, and an adjustable pulley portion 1414 rotatable relative to the base pulley portion 1412. At least one driving member (not pictured) may have a first end coupled to (e.g., at location "A") and wrap at least partially around the adjustable pulley portion 1414. Another driving member end may be coupled to (e.g., at location "B") and wrap at least partially around the base pulley portion 1412.

As shown in FIG. 14B, the adjustable pulley portion 1414 may include a plurality of openings 1415 by which fasteners may axially couple the adjustable pulley portion 1414 to the base pulley portion 1412. The plurality of openings 1415 may selectively align with one or more openings in the base pulley portion 1412. Each of the openings 1415, when aligned with an opening in the base pulley portion 1412, may correspond to a respective rotational position of the adjustable pulley portion 1414 relative to the base pulley portion 1412, and thus may correspond to a respective level of tension in the driving member. Similar to that in the pulley arrangement 1200 described above, the selected rotational position of the adjustable pulley portion 1414 may be locked by tightening a fastener or pin (not shown) in the aligned holes to thereby lock the tension of the driving member. Additionally or alternatively, the base pulley portion 1412 may include a plurality of openings that selectively align with one or more openings in the adjustable pulley portion 1414 so as to provide for multiple potential rotational positions of the adjustable pulley portion 1414 and tension levels in the driving member. In some variations, the adjustable pulley portion 1414 and/or the base pulley portion 1412 may include openings arranged akin to a Vernier scale to provide many options for discrete levels of tension in the driving member.

Angled Surface Pulleys

Figure 16A:
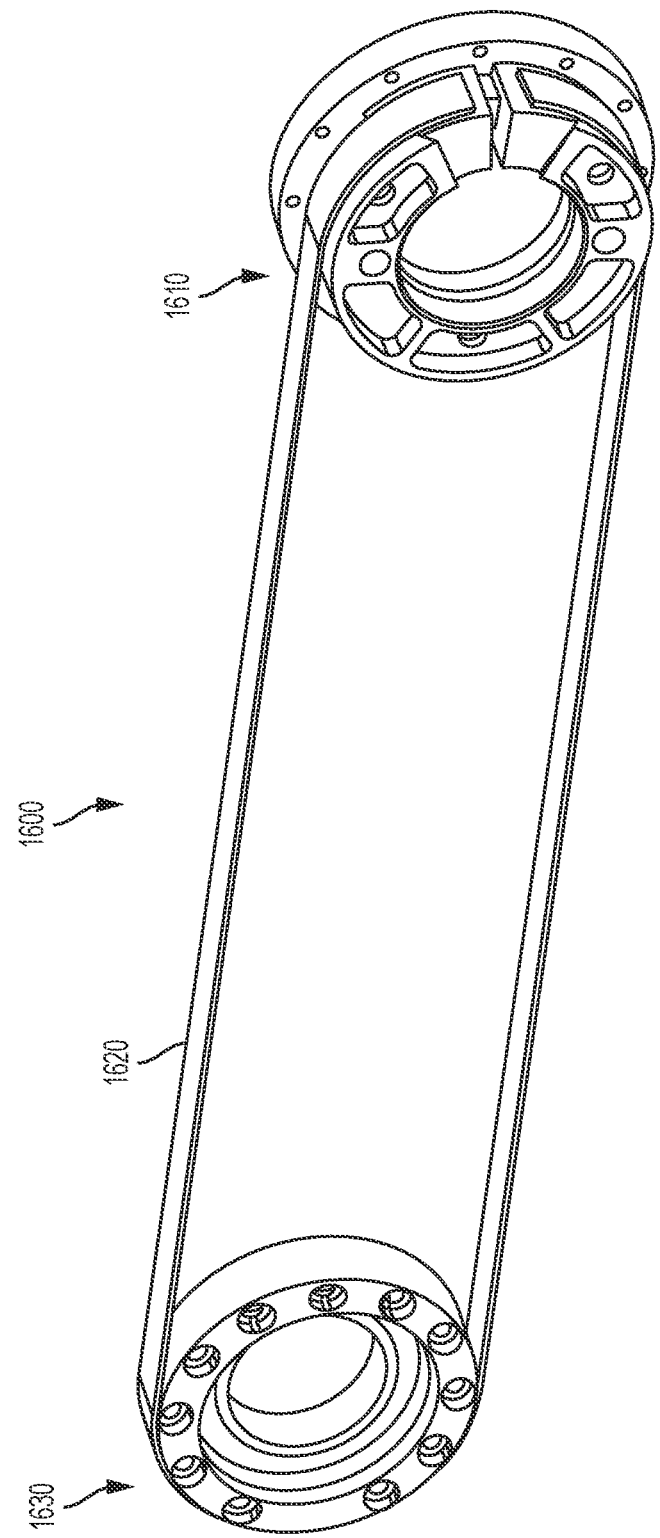
FIG. 16A is a perspective view of an exemplary variation of a pulley arrangement enabling tensioning of a driving member.

Another variation of a pulley arrangement 1600 is shown in FIGS. 16A and 16B. The pulley arrangement 1600 is similar to pulley arrangement 1200 shown in FIG. 12A except as described below, with similar numbering of elements. For example, the pulley arrangement 1600 may include an adjusting pulley 1610 and an idler pulley 1630 that are connected via at least one driving member 1620 (e.g., driving member 1620 and second driving member 1620'). Any suitable attachment mechanism or arrangement, including any of the driving member attachment variations described herein, may be used to couple an end of one or both driving members to the adjusting pulley and/or idler pulley. The pulley arrangements with adjusting pulleys described below may, for example, be used to adjust tension in the driving member in those variations in which the idler pulley may be a fixed distance from the base pulley portion (though in some variations the idler pulley position may be adjustable in distance from the base pulley portion, such as to further adjust tension in the driving member or members).

Figure 16F:
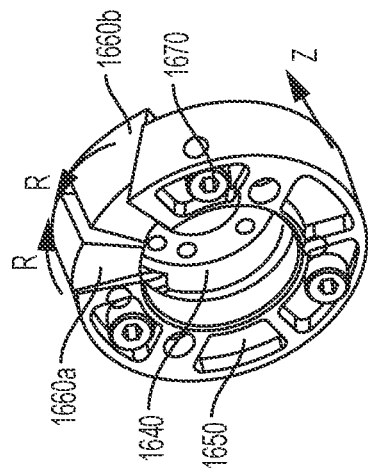
FIGS. 16E and 16F are perspective views of an exemplary adjusting pulley.
Figure 16I:
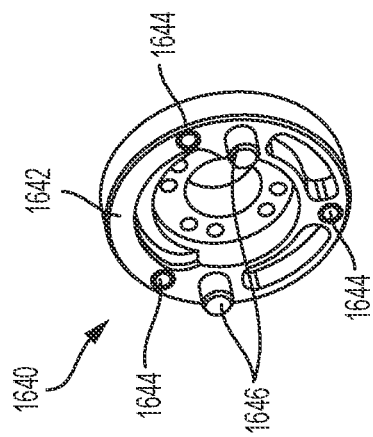
FIG. 16G-16I are perspective views of a sliding block, an adjustable pulley portion, and a base pulley portion, respectively, of an exemplary adjusting pulley.
Figure 16E:
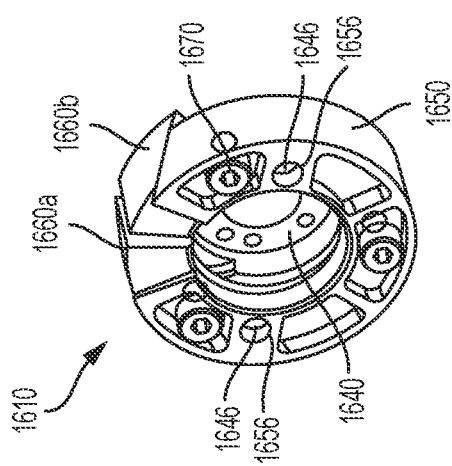

As shown in the exploded view of FIG. 16B and the assembled views of FIGS. 16E and 16F, the adjusting pulley 1610 may include a base pulley portion 1640 rotatable around an axis, an adjustable pulley portion 1650 coupled to the base pulley portion, and at least one sliding block (e.g., sliding blocks 1660a and 1660b) engaged with the adjustable pulley portion 1650. As shown in FIG. 16F, the adjustable pulley portion 1650 may be movable in a first direction (e.g., direction "Z") parallel to the axis of rotation of the base pulley portion 1640. The at least one sliding block may be configured to move in a second direction (e.g., direction "R") different from the first direction, in response to compression of the adjustable pulley portion 1650 against the base pulley portion 1640. In some variations, the first and second directions may be generally orthogonal to each other.

The base pulley portion 1640 may be configured to fixedly mount, for example, to a distal end of a pitch link (e.g., pitch link 1512 shown in FIG. 15A) or other portion of a robotic arm. As shown in FIG. 16I, the base pulley portion 1640 may have a mounting face configured to mate with the adjustable pulley portion 1650 and the sliding blocks 1660a and 1660b. The mounting face may, for example, include at least one ridge or other guide 1642 configured to engage the sliding blocks 1660a and 1660b. The base pulley portion 1640 may be a generally circular plate or disc as shown in FIG. 16I, but alternatively may have any suitable shape with one or more mounting features. In some variations, cutouts in the material of the base pulley portion 1640 may help reduce weight of the overall adjusting pulley assembly. The base pulley portion may be fitted with one or more pins 1646 configured to engage the holes 1656 in adjustable pulley portion 1650 such that the adjustable pulley portion 1650 rotates in 1:1 correspondence with the base pulley portion 1640. The pins 1646 may transfer torque from the base pulley portion 1640 to the adjustable pulley portion 1650, while allowing the adjustable pulley portion 1650 to move axially closer to and/or farther from the base pulley portion 1640.

Figure 16H:
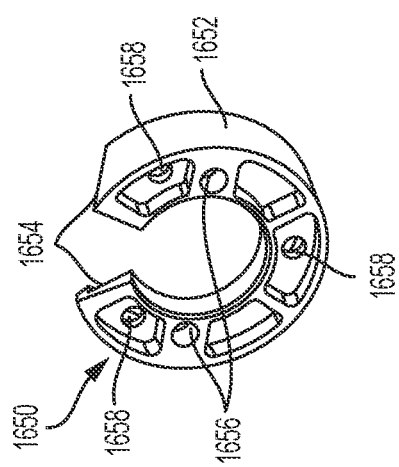

As shown in FIG. 16H, the adjustable pulley portion 1650 may be generally circular (e.g., ring or plate) and may have a driving region 1652 on an outer surface of the adjustable pulley portion 1650, around which one or more driven members are wrapped. The adjustable pulley portion 1650 may mate and couple with the mounting features of the base pulley portion 1640, such as with fasteners 1650 (e.g., screws) that pass through the holes 1658 of the adjustable pulley portion and engage threaded holes 1644 of the base pulley portion 1640. Additionally, the adjustable pulley portion 1650 may have an arcuate gap between spaced-apart surfaces 1654. Surfaces 1654 may be sloped (e.g., helical surfaces) in complementary fashion with sloped surfaces 1664 (e.g., helical surfaces) of sliding blocks 1660a and 1660b.

Figure 16G:
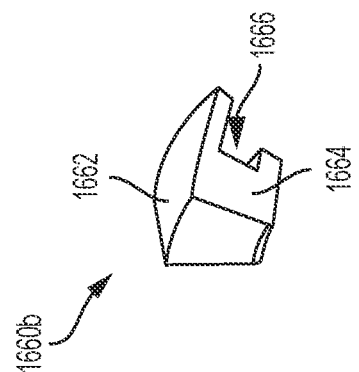

As shown in FIGS. 16E and 16F, the sliding blocks 1660a and 1660b may be disposed in the arcuate gap between spaced-apart surfaces 1654. Grooves 1666 of the sliding blocks may engage the outwardly-projecting guide 1642 on the base pulley portion (though alternatively, the guide 1642 may be a groove and the sliding blocks may include an outwardly-projecting guide). With reference to FIG. 16G, an end of a driving member may attached to a driving region 1662 on an outer surface of the sliding block 1660b. Similarly, an end of the same or another driving member may be attached to a driving region on an outer surface of the sliding block 1660a. The driving regions of the adjustable pulley portion 1650 and the sliding blocks 1660a and 1660b may be aligned so as to facilitate a smooth transition for a driving member to wrap around the driving regions.

The adjusting pulley 1610 may facilitate bilateral tensioning of the drive members 1620 and 1620. Generally, as shown in FIG. 16F, an input force may apply compression of the adjustable pulley portion 1650 against the base pulley portion 1640 and move the adjustable pulley portion 1650 in the direction "Z" (thereby bringing the adjustable pulley portion 1650 and the base pulley portion 1640 in closer approximation to each other). The input force may be applied by tightening the fasteners 1670 to tightening the adjustable pulley portion 1650 against the base pulley portion 1640. This axially-directed input force is translated, by sloped mating surfaces 1654 (on the adjustable pulley portion) and 1664 (on the sliding blocks), to move the sliding blocks circumferentially together. In other words, in response to this input force in the "Z" direction, the first and second sliding blocks 1660a and 1660b are configured to move circumferentially or arcuately toward each other in the "R" directions, thereby bringing the driving member ends (attached to the sliding blocks) together and applying tension to the driving member or members. If the helical surfaces 1664 on the sliding blocks are similar in slope, etc. (e.g., the sliding blocks 1660a and 1660b are mirror images of one another), then the sliding blocks 1660a and 1660b may move circumferentially or arcuately toward each other at about equal rates. If the helical surfaces 1664 on the sliding blocks are not similar in slope, then the sliding blocks 1660a and 1660b may move circumferentially or arcuately toward each other at different rates.

When a desired level of tensioning in the driving member or members is achieved with a particular axial position of the adjustable pulley portion 1650 relative to the base pulley portion 1640, one or more of the fasteners 1670 may be set to lock the tensioning level. For example, the axial position of the fasteners 1670 may be set with a locknut, jam nut with threadlocker, etc.

Therefore, a single input action of bringing the adjustable pulley portion and the base pulley portion closer together results in tightening the driving members, which may improve ease of setup and maintenance throughout the lifetime of the pulley mechanism. Additionally, with symmetrical sliding blocks, equal tension may be applied to both bands, which may improve load rating and lifetime of the pulley mechanism. Furthermore, within a single pulley arrangement including an adjustable pulley and an idler pulley, advantageously only one pulley may be required to provide adjustable termination of the bands.

Figure 17:
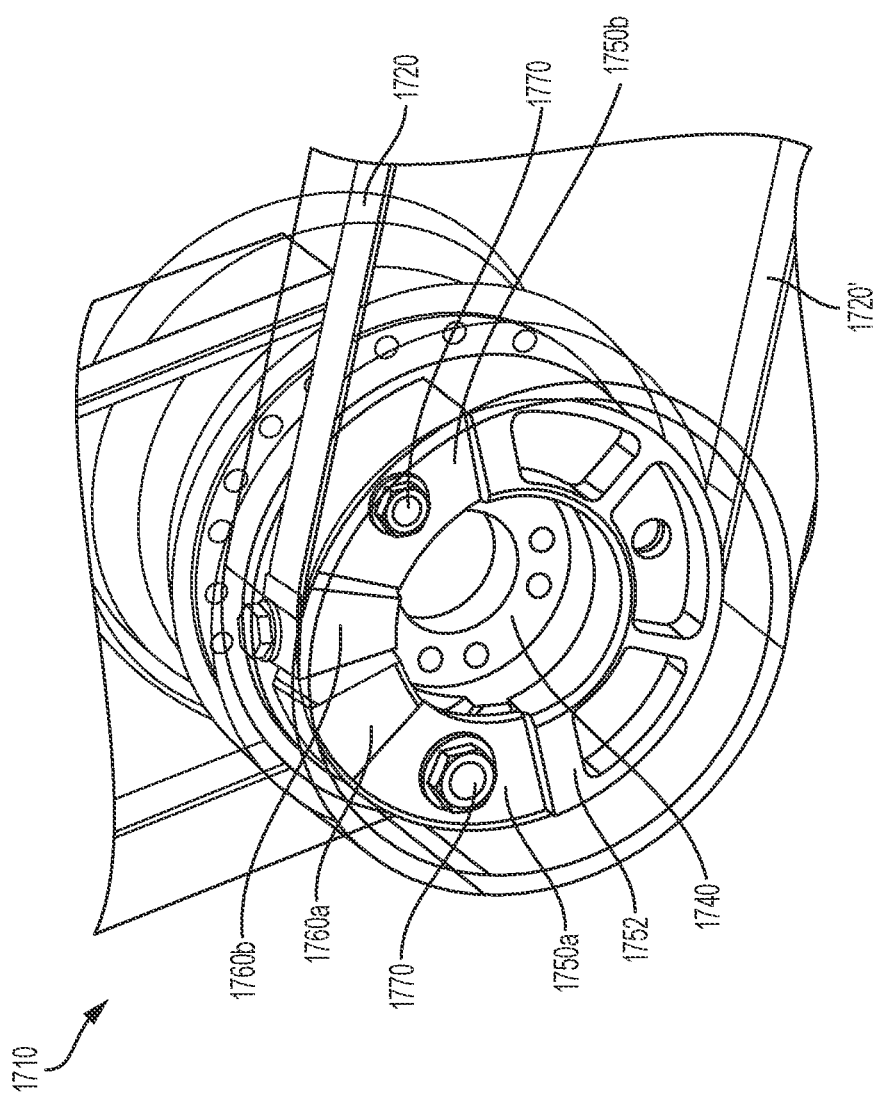
FIG. 17 is a perspective view of an exemplary variation of a pulley arrangement enabling tensioning of a driving member.

Another variation of an adjusting pulley 1710 is shown in FIG. 17. The adjusting pulley 1710 is similar to adjusting pulley 1610, except as described below, with similar numbering of elements. In the adjusting pulley 1710, the adjustable pulley portion includes two members 1750a and 1750b. The first member 1750a may be engaged with a first sliding block 1760a, and the second member 1750b may be engaged with a second sliding block 1760b. Similar to the adjustable pulley portion 1650 described above, the members 1750a and 1750b may be movable parallel to the axis around which the base pulley portion 1740 rotates. When the first member 1750a moves in such an axial direction toward the base pulley portion 1740, interfacing sloped (e.g., helical) surfaces of the first member 1750a and the first sliding block 1760a may translate into a circumferential or arcuate movement of the first sliding block 1760a toward the second sliding block 1760b. Similarly, when the second member 1750b moves in an axial direction toward the base pulley portion 1740, interfacing sloped (e.g., helical) surfaces of the second member 1760b and the second sliding block 1760b may translate into a circumferential or arcuate movement of the second sliding block 1760b toward the first sliding block 1760a. Therefore, like the adjusting pulley 1610 described above, a single input action of bringing the adjustable pulley portion and the base pulley portion closer together in the adjusting pulley 1710 results in tightening the driving members.

The members 1750a and 1750b may be moved independent of one another, which may enable independent tensioning of the driving member ends coupled to each member 1750a and 1750b. Furthermore, the members 1750a and 1750b may be moved in tandem, which may enable simultaneous tensioning of the driving member ends coupled to the members 1750a and 1750b.

When a desired level of tensioning in the driving member or members is achieved with a particular axial position of the adjustable pulley portion relative to the base pulley portion 1740, one or more of the fasteners 1770 may be set to lock the tensioning level. For example, the axial position of the fasteners 1770 may be set with a locknut, jam nut with threadlocker, etc.

Figure 18B:
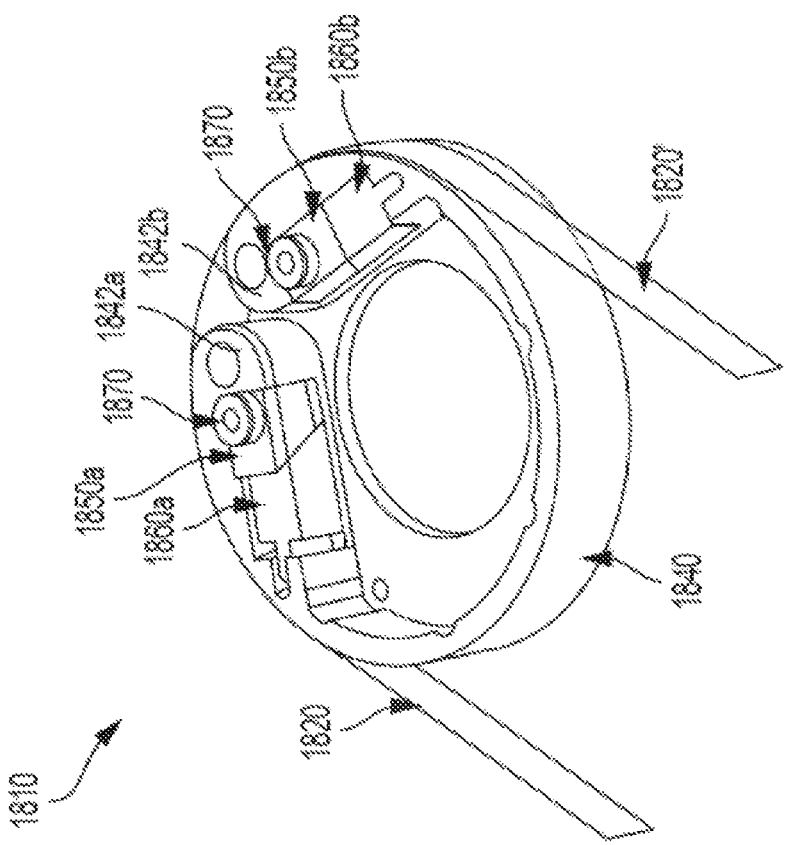
FIGS. 18A and 18B are side and perspective views, respectively, of an exemplary variation of a pulley arrangement enabling tensioning of a driving member.
Figure 18A:
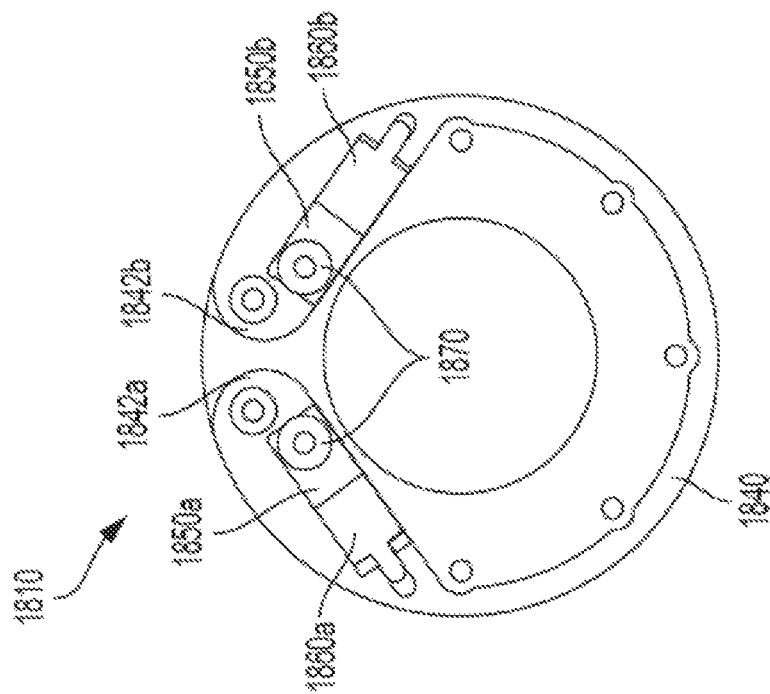

Another variation of an adjusting pulley 1810 is depicted in FIGS. 18A and 18B. The adjusting pulley 1810 is similar to adjusting pulley 1810, except as described below, with similar numbering of elements. In the adjusting pulley 1810, the adjustable pulley portion includes two members 1850a and 1850b, each of which is disposed in a recess of the base pulley portion 1840 such that the adjustable pulley portion and the base pulley portion 1840 are in-plane with each other (instead of generally adjacent to each other as in adjusting pulleys 1610 and 1710). The adjustable pulley portion members 1850a and 1850b may engage with first and second sliding blocks 1860a and 1860b, respectively. As shown in FIG. 18B, the end of driving member 1820 is wrapped around the base pulley portion, around a projection 1842a, over the adjustable pulley portion member 1850a, and is coupled to the first sliding block 1860a. Similarly, the end of driving member 1820' (or alternatively, a second end of driving member 1820) is wrapped around the base pulley portion, around a projection 1842b, over the adjustable pulley portion member 1850b, and is coupled to the second sliding block 1860b. The driving member ends may be coupled to the sliding blocks 1860a and 1860b using, for example, any of the attachment arrangements described herein, or any suitable attachment arrangement.

Similar to the adjustable pulley portion described above with respect to FIG. 17, the members 1850a and 1850b may be movable parallel to the axis around which the base pulley portion 1840 rotates. When the first member 1850a moves in such an axial direction toward the base pulley portion 1840, interfacing sloped (e.g., slanted, linearly slanted) surface of the first member 1850a and the first sliding block 1860a may translate into linear movement of the first sliding block 1860a in the recess away from the projection 1842a, thereby tensioning the end of driving member 1820. Similarly, when the second member 1850b moves in an axial direction toward the base pulley portion 1840, interfacing sloped (e.g., slanted, linearly slanted) surface of the second member 1850b and the second sliding block 1860b may translate into linear movement of the second sliding block 1860b in the recess away from the projection 1842b, thereby tensioning the end of driving member 1820'.

The members 1850a and 1850b may be moved independent of one another, which may enable independent tensioning of the driving member ends coupled to each member 1850a and 1850b. Furthermore, the members 1850a and 1850b may be moved in tandem, which may enable simultaneous tensioning of the driving member ends coupled to the members 1850a and 1850b. In some variations, during a process of tensioning, the driving members may be worked back and forth (by cyclically tensioning and slightly loosening the driving members) to distribute the tension across the length of the driving members.

When a desired level of tensioning in the driving member or members is achieved with a particular axial position of the adjustable pulley portion relative to the base pulley portion 1840, one or more of the fasteners 1870 may be set to lock the tensioning level. For example, the axial position of the fasteners 1870 may be set with a locknut, jam nut with threadlocker, etc.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, they thereby enable others skilled in the art to best utilize the invention and various embodiments with various modifications as are suited to the particular use contemplated. It is intended that the following claims and their equivalents define the scope of the invention.

What is claimed is:

1. A pulley arrangement, comprising:
   a base pulley portion rotatable around an axis;
   an adjustable pulley portion coupled to the base pulley portion and movable in a first direction parallel to the axis; and
   a first sliding block engaged with the adjustable pulley portion;
   wherein the first sliding block is configured to move in a second direction different from the first direction, in response to compression of the adjustable pulley portion against the base pulley portion.

2. The pulley arrangement of claim 1, further comprising a driving member comprising a first end coupled to the first sliding block, wherein at least a portion of the driving member is wrapped at least partially around the first sliding block.

3. The pulley arrangement of claim 2, wherein at least a portion of the driving member is wrapped at least partially around the adjustable pulley portion.

4. The pulley mechanism of claim 1, wherein the adjustable pulley portion includes at least one sloped surface engaged with the first sliding block.

5. The pulley mechanism of claim 4, wherein the sloped surface is a helical surface.

6. The pulley mechanism of claim 1, wherein the first sliding block includes at least one sloped surface.

7. The pulley mechanism of claim 6, wherein the sloped surface is a helical surface.

8. The pulley mechanism of claim 1, further comprising a second sliding block engaged with the adjustable pulley portion, wherein the first and second sliding blocks are disposed in an arcuate gap in the adjustable pulley portion and engaged with the adjustable pulley portion, wherein the first and second sliding blocks are configured to move circumferentially toward each other in response to compression of the adjustable pulley portion against the base pulley portion.

9. The pulley mechanism of claim 8, wherein the first and second sliding blocks are configured to move circumferentially toward each other at about equal rates in response to compression of the adjustable pulley portion against the base pulley portion.

10. The pulley mechanism of claim 8, wherein the first and second sliding blocks are disposed in an arcuate gap defined at least in part by the adjustable pulley portion.

11. The pulley mechanism of claim 8, further comprising a first driving member comprising a first end coupled to the first sliding block and a second driving member comprising a second end coupled to the second sliding block.

12. The pulley mechanism of claim 8, further comprising a driving member comprising a first end coupled to the first sliding block and a second end coupled to the second sliding block.

13. The pulley mechanism of claim 8, wherein the adjustable pulley portion comprises a first member engaged with the first sliding block and a second member engaged with the second sliding block, wherein the first and second members are movable in directions parallel to the axis.

14. The pulley mechanism of claim 1, wherein an axial position of the adjustable pulley portion relative to the base pulley portion is lockable.

15. The pulley mechanism of claim 14, wherein the axial position is lockable via one or more fasteners.

16. The pulley mechanism of claim 1, wherein the adjustable pulley portion is adjacent the base pulley portion.

17. The pulley mechanism of claim 1, wherein the first sliding block is configured to move in an arcuate path in response to compression of the adjustable pulley portion against the base pulley portion.

18. The pulley mechanism of claim 1, wherein the first sliding block is configured to move in a linear path in response to compression of the adjustable pulley portion against the base pulley portion.

19. The pulley mechanism of claim 1, wherein the adjustable pulley portion is disposed in a recess of the base pulley portion.

20. The pulley arrangement of claim 1, further comprising a second pulley, wherein at least one driving member wraps at least partially around the second pulley.

* * * * *

UNITED STATES PATENT AND TRADEMARK OFFICE
CERTIFICATE OF CORRECTION

PATENT NO. : 11,767,902 B2
APPLICATION NO. : 17/732842
DATED : September 26, 2023
INVENTOR(S) : Roman Devengenzo et al.

It is certified that error appears in the above-identified patent and that said Letters Patent is hereby corrected as shown below:

In the Claims

In Column 25, Line 42 of Claim 4, "The pulley mechanism" should read --The pulley arrangement--.
In Column 25, Line 45 of Claim 5, "The pulley mechanism" should read --The pulley arrangement--.
In Column 25, Line 47 of Claim 6, "The pulley mechanism" should read --The pulley arrangement--.
In Column 25, Line 49 of Claim 7, "The pulley mechanism" should read --The pulley arrangement--.
In Column 25, Line 51 of Claim 8, "The pulley mechanism" should read --The pulley arrangement--.
In Column 26, Line 8 of Claim 9, "The pulley mechanism" should read --The pulley arrangement--.
In Column 26, Line 13 of Claim 10, "The pulley mechanism" should read --The pulley arrangement--.
In Column 26, Line 16 of Claim 11, "The pulley mechanism" should read --The pulley arrangement--.
In Column 26, Line 20 of Claim 12, "The pulley mechanism" should read --The pulley arrangement--.
In Column 26, Line 24 of Claim 13, "The pulley mechanism" should read --The pulley arrangement--.
In Column 26, Line 29 of Claim 14, "The pulley mechanism" should read --The pulley arrangement--.
In Column 26, Line 32 of Claim 15, "The pulley mechanism" should read --The pulley arrangement--.
In Column 26, Line 34 of Claim 16, "The pulley mechanism" should read --The pulley arrangement--.
In Column 26, Line 36 of Claim 17, "The pulley mechanism" should read --The pulley arrangement--.
In Column 26, Line 40 of Claim 18, "The pulley mechanism" should read --The pulley arrangement--.
In Column 26, Line 44 of Claim 19, "The pulley mechanism" should read --The pulley arrangement--.

Signed and Sealed this
Twenty-first Day of November, 2023

Katherine Kelly Vidal
*Director of the United States Patent and Trademark Office*